United States Patent
Imamura et al.

(10) Patent No.: US 12,251,254 B2
(45) Date of Patent: Mar. 18, 2025

(54) CONSOLE FOR RADIOGRAPHY SYSTEM, METHOD FOR OPERATING CONSOLE FOR RADIOGRAPHY SYSTEM, AND OPERATION PROGRAM FOR CONSOLE FOR RADIOGRAPHY SYSTEM

(71) Applicant: FUJIFILM CORPORATION, Tokyo (JP)

(72) Inventors: Ryo Imamura, Kanagawa (JP); Kazuhiro Makino, Kanagawa (JP); Naoyuki Nishino, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 335 days.

(21) Appl. No.: 17/814,835

(22) Filed: Jul. 26, 2022

(65) Prior Publication Data
US 2022/0354447 A1     Nov. 10, 2022

Related U.S. Application Data

(63) Continuation of application No. PCT/JP2020/045330, filed on Dec. 4, 2020.

(30) Foreign Application Priority Data

Mar. 10, 2020   (JP) .................. 2020-041307

(51) Int. Cl.
*A61B 6/00*   (2024.01)
*A61B 6/46*   (2024.01)

(52) U.S. Cl.
CPC .......... *A61B 6/5217* (2013.01); *A61B 6/4405* (2013.01); *A61B 6/4488* (2013.01)

(58) Field of Classification Search
None
See application file for complete search history.

(56) References Cited

U.S. PATENT DOCUMENTS

2004/0146190 A1    7/2004  Kasai
2004/0196959 A1 * 10/2004 Weston .................... H05G 1/02
                                                                    378/141
(Continued)

FOREIGN PATENT DOCUMENTS

CN    103616874 A  *  3/2014
CN    104812304 A     7/2015
(Continued)

OTHER PUBLICATIONS

International Search Report issued in International Application No. PCT/JP2020/045330 on Feb. 2, 2021.
(Continued)

*Primary Examiner* — Mohammed Rachedine
(74) *Attorney, Agent, or Firm* — SOLARIS Intellectual Property Group, PLLC

(57) ABSTRACT

A console for a radiography system includes at least one processor configured to execute display-related processing of displaying, at an imaging site, a radiographic image obtained by radiography, the display-related processing including reception processing of receiving the radiographic image from a radiographic image detection device and image processing of processing the received radiographic image to a radiographic image for display, computer aided diagnosis processing on the radiographic image after the image processing, and priority processing of giving priority to the display-related processing over the computer aided diagnosis processing in a case where the display-related processing and the computer aided diagnosis processing compete with each other.

17 Claims, 35 Drawing Sheets

(56) References Cited

U.S. PATENT DOCUMENTS

| | | | |
|---|---|---|---|
| 2010/0239065 A1* | 9/2010 | Tsubota | G03B 42/04 378/62 |
| 2014/0211922 A1 | 7/2014 | Kuwabara et al. | |
| 2015/0265223 A1 | 9/2015 | Simon et al. | |
| 2016/0256119 A1 | 9/2016 | Nakayama et al. | |
| 2017/0273652 A1* | 9/2017 | Tajima | G16H 50/30 |
| 2019/0076109 A1* | 3/2019 | Uehara | G01T 1/161 |
| 2021/0134442 A1* | 5/2021 | Ahn | G16H 30/40 |

FOREIGN PATENT DOCUMENTS

| | | | |
|---|---|---|---|
| JP | 2003-116838 A | | 4/2003 |
| JP | 2004-222982 A | | 8/2004 |
| JP | 2010-172558 A | | 8/2010 |
| JP | 2011-115265 A | | 6/2011 |
| JP | 2013-188488 A | | 9/2013 |
| JP | 2016-501080 A | | 1/2016 |
| JP | 2017108850 A | * | 6/2017 |
| JP | 2019-013843 A | | 1/2019 |
| JP | 2020-030694 A | | 2/2020 |
| WO | 2013/047489 A1 | | 4/2013 |
| WO | 2015/076067 A1 | | 5/2015 |
| WO | WO-2017054974 A1 * | 4/2017 | ........... A61B 6/4405 |

OTHER PUBLICATIONS

Written Opinion of the ISA issued in International Application No. PCT/JP2020/045330 on Feb. 2, 2021.

English language translation of the following: Office action dated Aug. 28, 2024 from the SIPO in a Chinese patent application No. 202080097055.2 corresponding to the instant patent application. This office action translation is submitted now in order to supplement the understanding of the cited references which are being disclosed in the instant Information Disclosure Statement.

English language translation of the following: Office action dated Jun. 20, 2023 from the JPO in a Japanese patent application No. 2022-505763 corresponding to the instant patent application.

* cited by examiner

| IMAGING MENU | IRRADIATION CONDITION |
|---|---|
| FRONT CHEST DECUBITUS  BODY SHAPE SMALL | TUBE VOLTAGE 150 kV   TUBE CURRENT 20 mA   IRRADIATION TIME 10 ms |
| FRONT CHEST DECUBITUS  BODY SHAPE MEDIUM | TUBE VOLTAGE 150 kV   TUBE CURRENT 25 mA   IRRADIATION TIME 10 ms |
| FRONT CHEST DECUBITUS  BODY SHAPE LARGE | TUBE VOLTAGE 150 kV   TUBE CURRENT 30 mA   IRRADIATION TIME 10 ms |
| ⋮ | ⋮ |

CONSOLE FOR RADIOGRAPHY SYSTEM, METHOD FOR OPERATING CONSOLE FOR RADIOGRAPHY SYSTEM, AND OPERATION PROGRAM FOR CONSOLE FOR RADIOGRAPHY SYSTEM

CROSS-REFERENCE TO RELATED APPLICATIONS

This application is a continuation application of International Application No. PCT/JP2020/045330 filed on Dec. 4, 2020, the disclosure of which is incorporated herein by reference in its entirety. Further, this application claims priority from Japanese Patent Application No. 2020-041307 filed on Mar. 10, 2020, the disclosure of which is incorporated herein by reference in its entirety.

BACKGROUND

1. Technical Field

A technique of the present disclosure relates to a console for a radiography system, a method for operating a console for a radiography system, and an operation program for a console for a radiography system.

2. Description of the Related Art

In a medical field, diagnosis using a radiographic image captured with a radiography system has been actively performed. The radiography system includes a radiation generation unit that emits radiation, a radiographic image detection device, and a console. The radiographic image detection device receives radiation emitted from the radiation generation unit and transmitted through a subject and outputs the radiographic image. The console receives the radiographic image from the radiographic image detection device and carries out image processing on the received radiographic image. The radiographic image after the image processing is instantly displayed on a display at an imaging site to allow an operator to check a reflected state.

Incidentally, in the related art, a method of carrying out computer aided diagnosis (CAD) processing on a radiographic image to extract a candidate of a lesion, such as a tumor, reflected in the radiographic image is performed (WO2015/076067A). In a radiography system described in WO2015/076067A, a console (written as an imaging apparatus control unit in WO2015/076067A) has a function of CAD processing.

SUMMARY

Like the radiography system described in WO2015/076067A, in a case where the console has the function of the CAD processing, the following problem may occur. That is, to allow an operator to check a reflected state of a radiographic image, in a case where a series of processing (hereinafter, referred to as display-related processing) of receiving the radiographic image from a radiographic image detection device and executing image processing on the received radiographic image competes with the CAD processing, the display-related processing may be delayed due to the CAD processing having a comparatively large processing load. In a case where the display-related processing is delayed, for example, the radiographic image is hardly normally received or the image processing hardly proceeds and the display of the radiographic image is hindered.

An object of the technique of the present disclosure is to provide a console for a radiography system, a method for operating a console for a radiography system, and an operation program for a console for a radiography system capable of allowing an operator to check a reflected state of a radiographic image without hindrance.

To achieve the above-described object, there is provided a console for a radiography system of the present disclosure comprising at least one processor configured to execute display-related processing of displaying, at an imaging site, a radiographic image obtained by radiography, the display-related processing including reception processing of receiving the radiographic image from a radiographic image detection device and image processing of processing the received radiographic image to a radiographic image for display, computer aided diagnosis processing on the radiographic image after the image processing, and priority processing of giving priority to the display-related processing over the computer aided diagnosis processing in a case where the display-related processing and the computer aided diagnosis processing compete with each other.

It is preferable that the processor is configured to prohibit the execution of the computer aided diagnosis processing while the display-related processing is being executed, as the priority processing.

It is preferable that the processor is configured to not start the computer aided diagnosis processing on present imaging in a case where the display-related processing on next imaging starts in a period from when the display-related processing on the present imaging ends to when the computer aided diagnosis processing on the present imaging subsequently automatically starts.

It is preferable that the processor is configured to interrupt the computer aided diagnosis processing on first imaging and start the display-related processing on second imaging after the first imaging, as the priority processing.

It is preferable that the processor is configured to automatically resume the interrupted computer aided diagnosis processing on the first imaging after the display-related processing on the second imaging ends.

It is preferable that the processor is configured to receive a selection instruction from an operator regarding whether or not to resume the interrupted computer aided diagnosis processing on the first imaging after the display-related processing on the second imaging ends, resume the interrupted computer aided diagnosis processing on the first imaging in a case where a selection instruction to resume the interrupted computer aided diagnosis processing is received, and not resume the interrupted computer aided diagnosis processing on the first imaging in a case where a selection instruction not to resume the interrupted computer aided diagnosis processing is received.

It is preferable that the processor is configured to resume the interrupted computer aided diagnosis processing on the first imaging in a case where the second imaging is not reimaging of the first imaging, and not resume the interrupted computer aided diagnosis processing on the first imaging in a case where the second imaging is the reimaging.

It is preferable that the processor is configured to determine that the second imaging is not the reimaging in a case where an imaging part is not the same as in the first imaging and resume the interrupted computer aided diagnosis processing on the first imaging, and determine that the second imaging is the reimaging in a case where the imaging part is the same as in the first imaging and not resume the interrupted computer aided diagnosis processing on the first imaging.

It is preferable that the processor is configured to notify an operator that the computer aided diagnosis processing on the first imaging is interrupted.

It is preferable that the processor is configured to allocate a part of resources allocated to the computer aided diagnosis processing on first imaging to the display-related processing on second imaging after the first imaging and set the number of resources allocated to the display-related processing on the second imaging greater than in the computer aided diagnosis processing on the first imaging, as the priority processing.

It is preferable that the processor is configured to receive an execution instruction of the computer aided diagnosis processing from an operator.

It is preferable that the processor that executes the display-related processing and the computer aided diagnosis processing is one processor.

It is preferable that the processor has two sub-processors of a first sub-processor that executes the display-related processing and a second sub-processor that executes the computer aided diagnosis processing.

It is preferable that the processor is configured to start the display-related processing at a start timing of the reception processing.

Alternatively, it is preferable that the processor is configured to start the display-related processing at a timing of transmitting an irradiation start synchronization signal for informing of an irradiation start of radiation to the radiographic image detection device.

It is preferable that the console for a radiography system further comprises a cooling mechanism that cools the processor, and the processor is configured to set a cooling level of the cooling mechanism higher than in a normal state at least while the computer aided diagnosis processing is being executed.

It is preferable that the console for a radiography system is mounted in a mobile radiation generation apparatus that has a radiation generation unit configured to emit radiation and is driven with a battery in a wireless manner.

There is provided a method for operating a console for a radiography system of the present disclosure comprising a display-related processing step of executing display-related processing of displaying, at an imaging site, a radiographic image obtained by radiography, the display-related processing including reception processing of receiving the radiographic image from a radiographic image detection device and image processing of processing the received radiographic image to a radiographic image for display, a computer aided diagnosis processing step of executing computer aided diagnosis processing on the radiographic image after the image processing, and a priority processing step of giving priority to the display-related processing over the computer aided diagnosis processing in a case where the display-related processing and the computer aided diagnosis processing compete with each other.

There is provided an operation program for a console for a radiography system of the present disclosure, the operation program causing a computer to function as a display-related processing unit that executes display-related processing of displaying, at an imaging site, a radiographic image obtained by radiography, the display-related processing including reception processing of receiving the radiographic image from a radiographic image detection device and image processing of processing the received radiographic image to a radiographic image for display, a computer aided diagnosis processing unit that executes computer aided diagnosis processing on the radiographic image after the image processing, and a priority processing unit that gives priority to the display-related processing over the computer aided diagnosis processing in a case where the display-related processing and the computer aided diagnosis processing compete with each other.

According to the technique of the present disclosure, it is possible to provide a console for a radiography system, a method for operating a console for a radiography system, and an operation program for a console for a radiography system capable of allowing an operator to a reflected state of a radiographic image without hindrance.

BRIEF DESCRIPTION OF THE DRAWINGS

Exemplary embodiments according to the technique of the present disclosure will be described in detail based on the following figures, wherein.

DETAILED DESCRIPTION

First Embodiment

Figure 1:
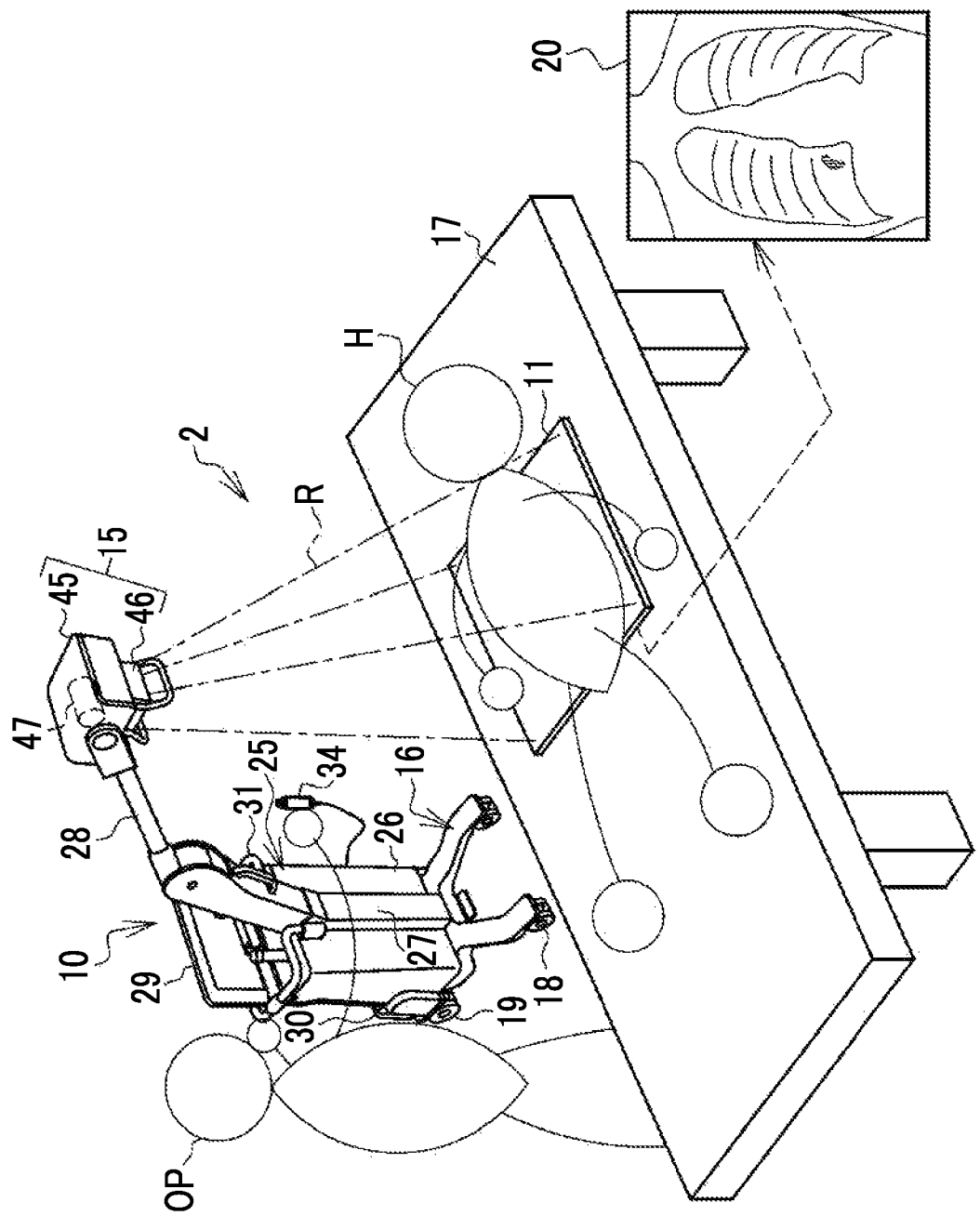
FIG. 1 is a diagram showing a manner of imaging using a radiography system.
Figure 2:
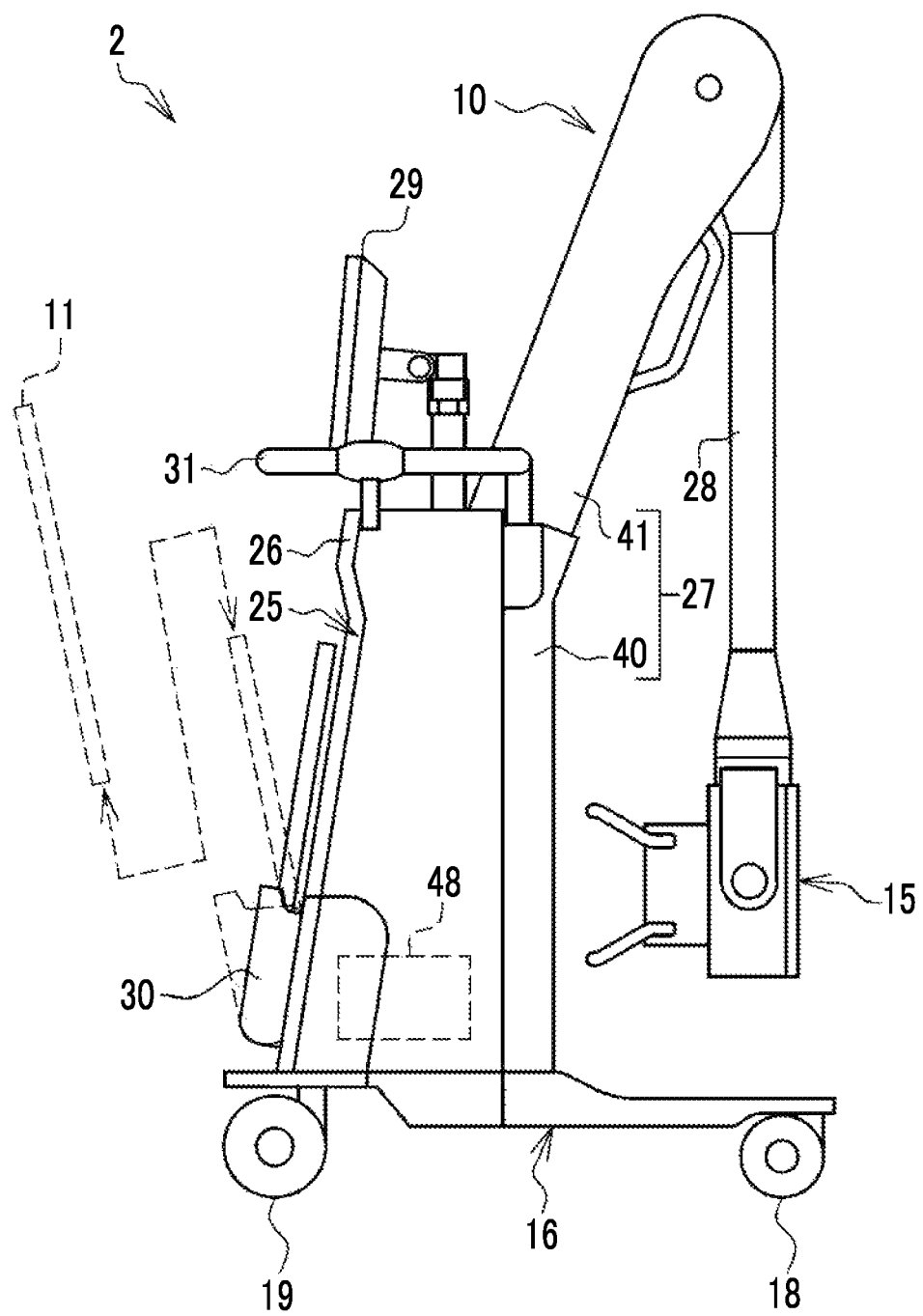
FIG. 2 is a diagram showing a radiography system.

In FIGS. 1 and 2, a radiography system 2 comprises a mobile radiation generation apparatus 10 and an electronic cassette 11. The mobile radiation generation apparatus 10 has a radiation generation unit 15 and a carriage 16. The radiation generation unit 15 emits radiation R toward a subject H who lies on a bed 17, for example. The carriage 16 has a pair of right and left front wheels 18 and a pair of right and left rear wheels 19. The mobile radiation generation apparatus 10 is movable inside a hospital by the carriage 16. The mobile radiation generation apparatus 10 is used in so-called round imaging for imaging the subject H while visiting patient's rooms. For this reason, the mobile radiation generation apparatus 10 is also referred to as a treatment cart. The mobile radiation generation apparatus 10 can also be carried to an operation room and used in the middle of an operation. In addition, the mobile radiation generation apparatus 10 can also be carried in an outdoor disaster site and used in emergency.

As well known in the art, the electronic cassette 11 is a radiographic image detection device that is a sensor panel incorporated in a portable housing and is driven by a battery in a wireless manner. As is also well known, the sensor panel has a configuration in which a plurality of pixels that are sensitive to the radiation R or visible light converted from the radiation R to generate signal charge are arranged. The electronic cassette 11 is placed, for example, below the subject H, receives the radiation R emitted from the radiation generation unit 15 and transmitted through the subject H, and outputs a radiographic image 20.

A body portion 25 is mounted on the carriage 16. The body portion 25 includes a center portion 26, a column portion 27, an arm portion 28, and the like in addition to the above-described radiation generation unit 15.

Figure 3:
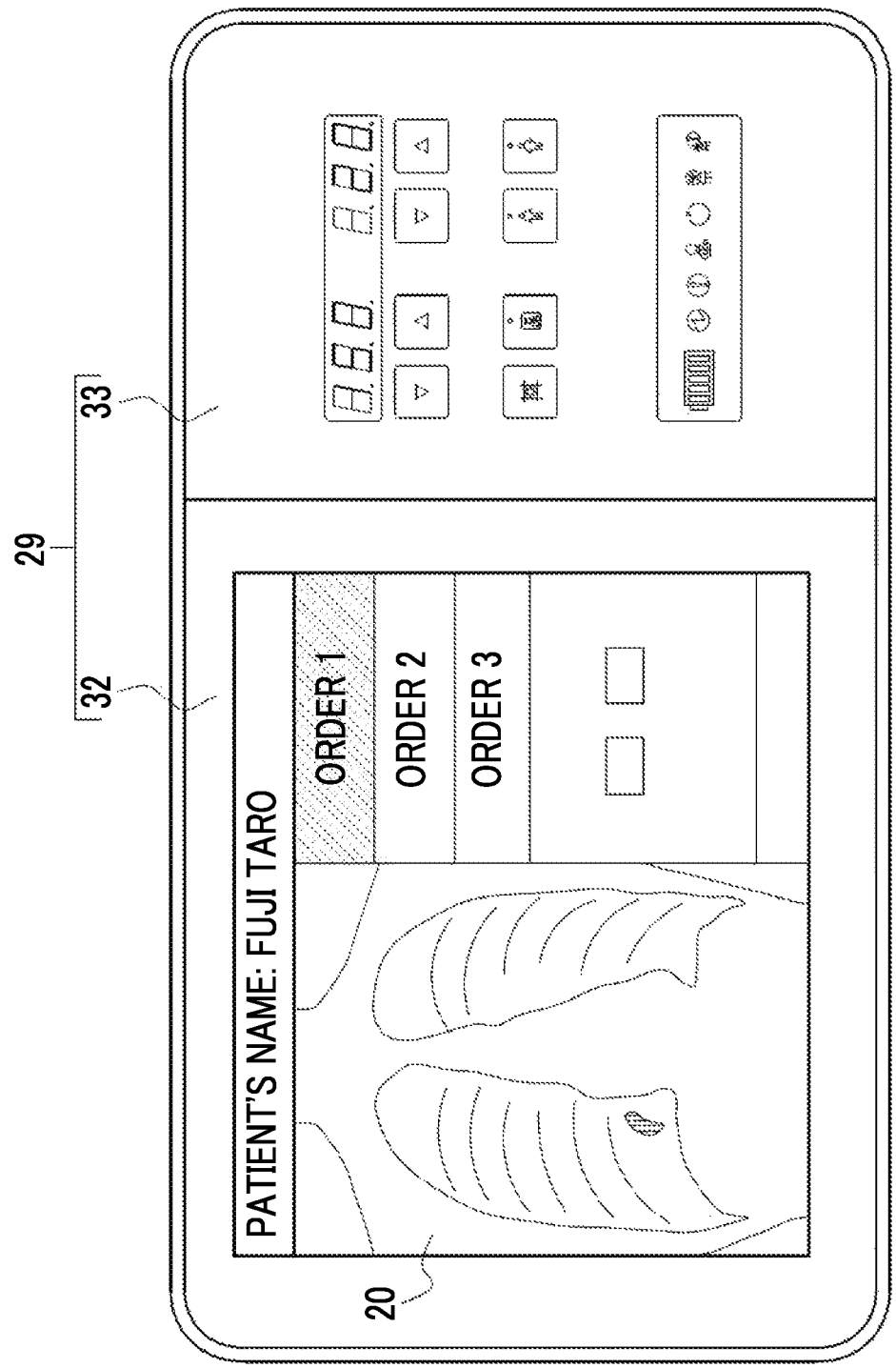
FIG. 3 is a diagram showing a UI-based device.

The center portion 26 has a user interface (UI)-based device 29, a cassette storage portion 30, and a handle 31. The UI-based device 29 is configured with, as shown in FIG. 3, a touch panel display 32 (hereinafter, simply referred to as a display) and an operation panel 33. The display 32 displays the radiographic image 20 and the like. The operation panel 33 is operated by an operator OP, such as a radiographer, in setting irradiation conditions 76 (see FIG. 5) of the radiation R, or the like.

The cassette storage portion 30 is provided on a rear portion side of the center portion 26. The cassette storage portion 30 stores the electronic cassette 11. There are a plurality of kinds of electronic cassettes 11 having a longitudinal/lateral size of 17 inches×17 inches, 17 inches×14 inches, 12 inches×10 inches, and the like. The cassette storage portion 30 can store a plurality of kinds of electronic cassettes 11 regardless of the kinds. The cassette storage portion 30 has a function of charging a battery of the stored electronic cassette 11.

The handle 31 is provided to surround above the center portion 26. The handle 31 is held by the operator OP to operate not only the carriage 16 but also the mobile radiation generation apparatus 10. The operator OP runs the mobile radiation generation apparatus 10 while holding the handle 31 in a state shown in FIG. 2 in which the radiation generation unit 15 is stored above the carriage 16 and in front of the center portion 26.

An irradiation switch 34 is attached to the center portion 26. The irradiation switch 34 is a switch that is provided to allow the operator OP to give an instruction to start irradiation of radiation. An extension cable is connected to the irradiation switch 34 and can be detached from the center portion 26 for use. The irradiation switch 34 is, for example, a two-stage push switch. The irradiation switch 34 generates a warm-up instruction signal 77 (see FIG. 5) when being pushed to the first stage (half-pushed), and generates an irradiation start instruction signal 78 (see FIG. 5) when being pushed to the second stage (fully pushed).

The column portion 27 has a prismatic columnar shape and is provided upright at the center of the carriage 16. The arm portion 28 has a proximal end that is attached to the column portion 27, and a distal end that is a free end on an opposite side to the proximal end and to which the radiation generation unit 15 is attached.

The column portion 27 has a first column 40 and a second column 41 that is consecutively provided upward at a predetermined angle from the first column 40. The first column 40 is provided on an upper surface of the carriage 16. The second column 41 can rotate with respect to the first column 40 with a vertical axis as a rotation axis.

The arm portion 28 can be bent with respect to the second column 41 or can extend in a direction along the second column 41. The radiation generation unit 15 can swing front and back with respect to the arm portion 28.

The radiation generation unit 15 is configured with a radiation source 45 and an irradiation field limiter 46. A radiation tube 47 is incorporated in the radiation source 45. The radiation tube 47 generates, for example, X-rays as the radiation R. The radiation tube 47 is provided with a filament, a target, a grid electrode, and the like (all are not shown). A voltage from a voltage generator 48 incorporated in the center portion 26 is applied between the filament as a cathode and the target as an anode. The voltage that is applied between the filament and the target is referred to as a tube voltage. The filament discharges thermoelectrons according to the applied tube voltage toward the target. The target radiates radiation R with collision of the thermoelectrons from the filament. The grid electrode is disposed between the filament and the target. The grid electrode changes a flow rate of the thermoelectrons from the filament toward the target according to the voltage applied from the voltage generator 48. The flow rate of the thermoelectrons from the filament toward the target is referred to as a tube current. The tube voltage and the tube current are set as irradiation conditions 76 along with an irradiation time.

In a case where the irradiation switch 34 is half-pushed and the warm-up instruction signal 77 is generated, the filament is warmed up and the rotation of the target is started. When the filament reaches a prescribed temperature, and the target reaches a prescribed rotation speed, warm-up is completed. In a case where the irradiation switch 34 is fully pushed and the irradiation start instruction signal 78 is generated in a state in which the warm-up is completed, the tube voltage is applied from the voltage generator 48, and radiation R is generated from the radiation tube 47. When the irradiation time set in the irradiation conditions 76 has elapsed from the start of generation of radiation R, the application of the tube voltage is stopped, and irradiation of radiation R is ended.

The irradiation field limiter 46 limits an irradiation field of radiation R generated from the radiation tube 47. For example, the irradiation field limiter 46 has a configuration in which four shield plates formed of lead or the like shielding radiation R are disposed on respective sides of a quadrangle, and an emission opening of the quadrangle transmitting radiation is formed in a center portion. The irradiation field limiter 46 changes the positions of the shield plates to change the size of the emission opening, and accordingly, changes the irradiation field of radiation R.

Figure 4:
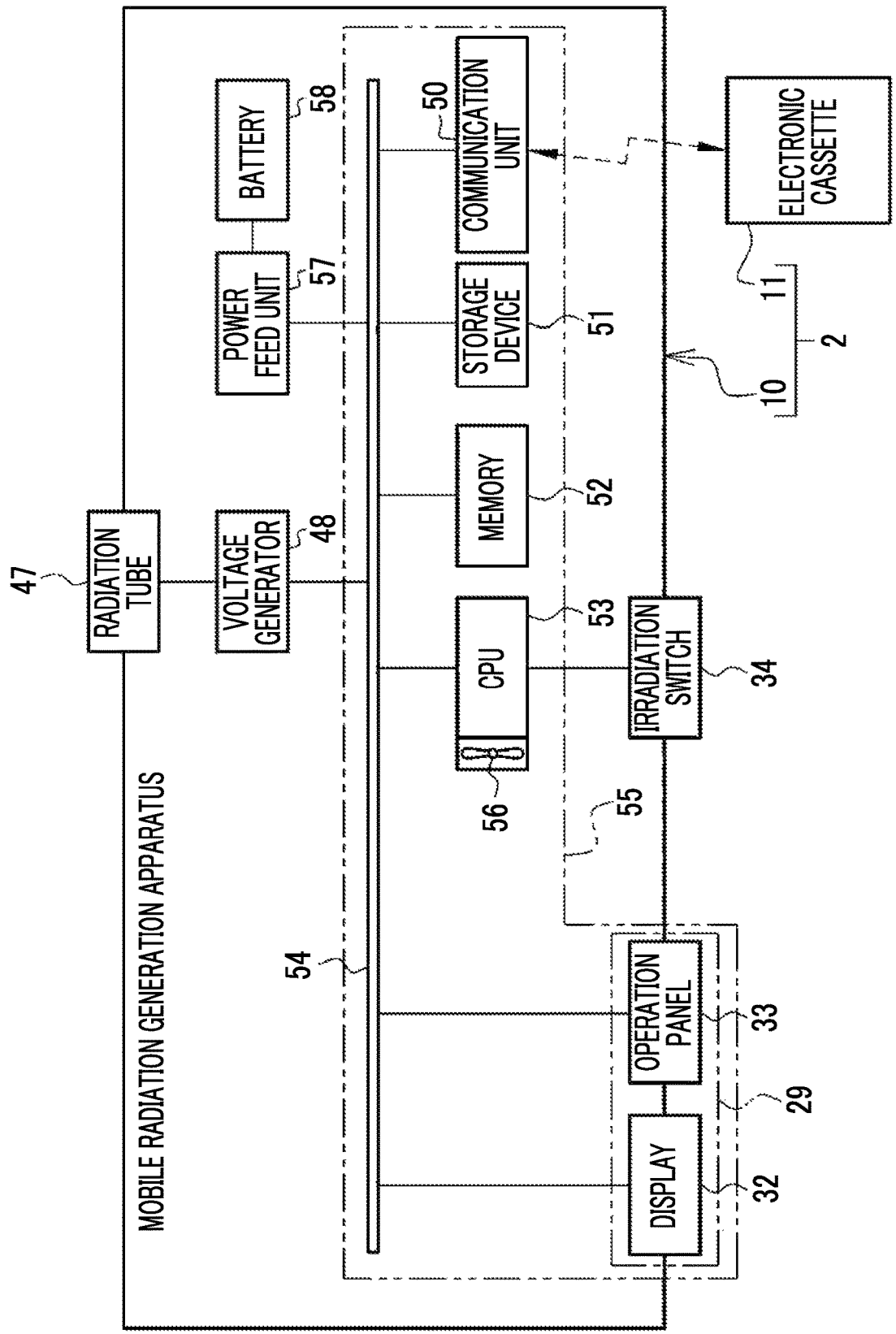
FIG. 4 is a block diagram of a mobile radiation generation apparatus.

In FIG. 4, the mobile radiation generation apparatus 10 has a communication unit 50, a storage device 51, a memory 52, a central processing unit (CPU) 53, and the like. The communication unit 50, the storage device 51, the memory 52, the CPU 53, and the like are connected through a busline 54. The UI-based device 29 and the voltage generator 48 are also connected to the busline 54. The communication unit 50, the storage device 51, the memory 52, the CPU 53, the busline 54, and the UI-based device 29 configure a console 55. The console 55 is an example of "a console for a radiography system" according to the technique of the present disclosure. The storage device 51, the memory 52, the CPU 53, and the busline 54 are an example of a "computer" according to the technique of the present disclosure. The CPU 53 is an example of a "processor" according to the technique of the present disclosure.

The communication unit 50 includes a wireless communication interface that performs wireless communication with the electronic cassette 11. The communication unit 50 includes a network interface that performs wireless communication with an external device other than the electronic cassette 11 through a network. Examples of the external device include a radiology information system (RIS) that manages information, such as an imaging order, and picture archiving and communication systems (PACS). Examples of the network include a wide area network (WAN), such as the Internet or a public communication network.

The storage device 51 is, for example, a hard disk drive or a solid state drive, and stores various programs and various kinds of data associated with various programs. The memory 52 is a work memory on which the CPU 53 executes processing. The CPU 53 reads out a program stored in the storage device 51 to the memory 52 and executes processing depending on the read program. With this, the CPU 53 integrally controls the operations of the units of the mobile radiation generation apparatus 10.

The above-described irradiation switch 34 is connected to the CPU 53. The irradiation switch 34 outputs the warm-up instruction signal 77 and the irradiation start instruction signal 78 to the CPU 53. A cooling fan 56 is attached to the CPU 53. The cooling fan 56 is an example of a "cooling mechanism" according to the technique of the present disclosure.

A power feed unit 57 is connected to the busline 54. The power feed unit 57 supplies electric power from a battery 58 to the units of the mobile radiation generation apparatus 10. The power feed unit 57 includes a direct-current (DC)-DC converter that converts a direct-current voltage from the battery 58 to a voltage having a value depending on a supply destination, a voltage stabilization circuit that stabilizes the value of the converted voltage, and the like. The battery 58 is incorporated in, for example, the center portion 26. In this way, the mobile radiation generation apparatus 10 is driven with the battery 58 in a wireless manner. The mobile radiation generation apparatus 10 can connect a plug (not shown) of a power cord extending from a lower portion of the body portion 25 to a socket of a commercial power supply to charge the battery 58 or can operate with electric power from the commercial power supply.

Figure 5:
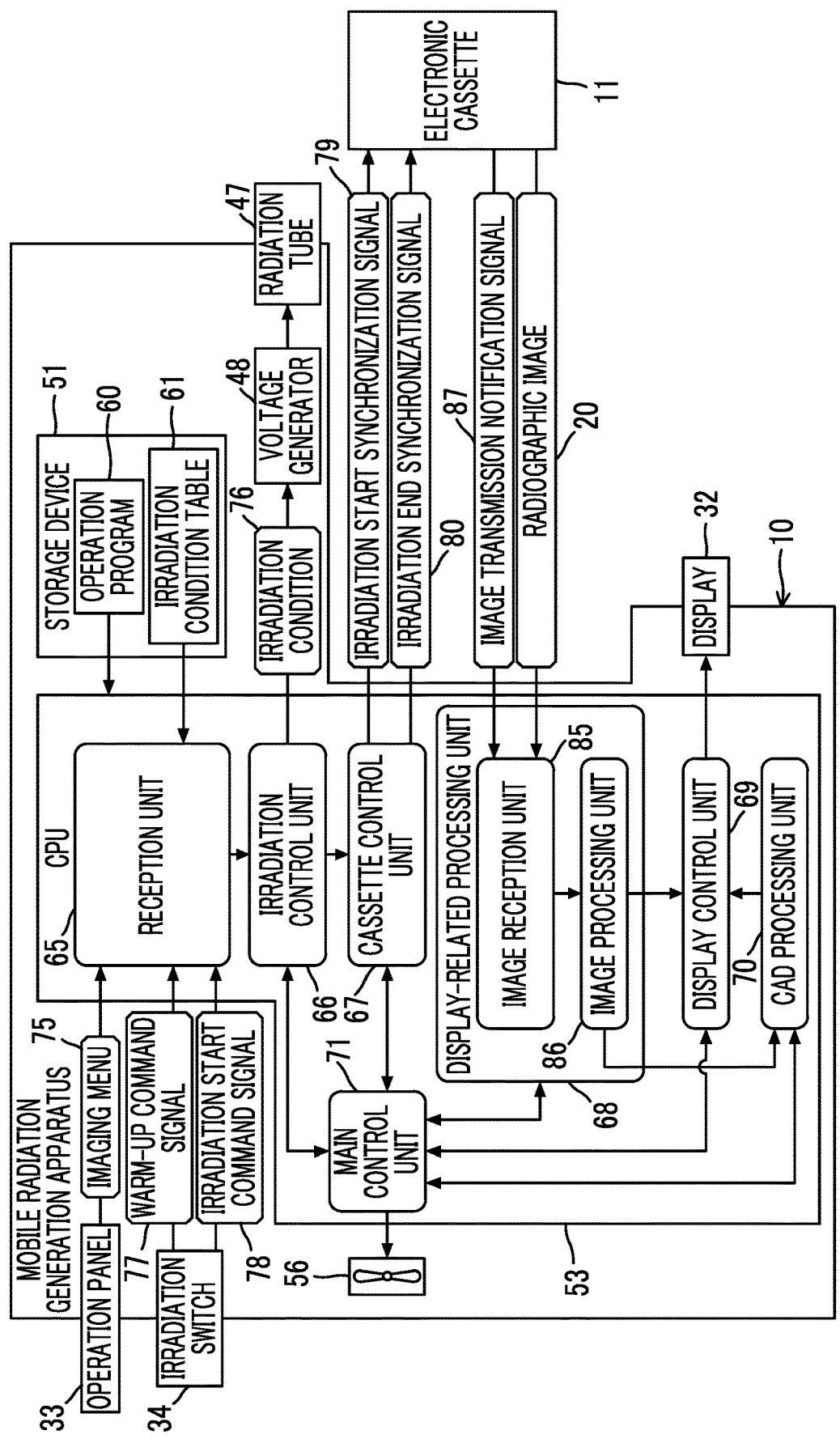
FIG. 5 is a block diagram showing functions of a CPU of a console.

In FIG. 5, an operation program 60 is stored in the storage device 51. The operation program 60 is a program that causes a computer configured with the storage device 51, the memory 52, the CPU 53, and the busline 54 to operate as "a console for a radiography system" according to the technique of the present disclosure. That is, the operation program 60 is an example of "an operation program for a console for a radiography system" according to the technique of the present disclosure. An irradiation condition table 61 is also stored in the storage device 51.

The CPU 53 executes the operation program 60 to function as a reception unit 65, an irradiation control unit 66, a cassette control unit 67, a display-related processing unit 68, a display control unit 69, a computer aided diagnosis processing unit (hereinafter, referred to as a CAD processing unit) 70, and a main control unit 71 in cooperation with the memory 52 and the like.

The reception unit 65 receives an imaging menu 75 input from the operator OP through the operation panel 33. The reception unit 65 reads out the irradiation conditions 76 corresponding to the received imaging menu 75 from the irradiation condition table 61 and outputs the read-out irradiation condition 76 to the irradiation control unit 66.

The reception unit 65 also receives the warm-up instruction signal 77 and the irradiation start instruction signal 78 from the irradiation switch 34. The reception unit 65 outputs the reception of the warm-up instruction signal 77 and the reception of the irradiation start instruction signal 78 to the irradiation control unit 66.

The irradiation control unit 66 controls the operation of the radiation tube 47 to control irradiation of the radiation R. The irradiation control unit 66 sets the irradiation conditions 76 in the voltage generator 48. The irradiation control unit 66 makes the radiation tube 47 perform warm-up in a case where the reception of the warm-up instruction signal 77 is input from the reception unit 65. Furthermore, the irradiation control unit 66 causes the irradiation of the radiation R from the radiation tube 47 through the voltage generator 48 under the set irradiation conditions 76 in a case where the reception of the irradiation start instruction signal 78 is input from the reception unit 65.

The irradiation control unit 66 outputs the start of the irradiation of the radiation R to the cassette control unit 67 in conformity with an irradiation start timing of the radiation R. Furthermore, the irradiation control unit 66 outputs the end of the irradiation of the radiation R to the cassette control unit 67 in conformity with an irradiation end timing of the radiation R.

The cassette control unit 67 transmits various control signals to the electronic cassette 11 through the communication unit 50 to control the operation of the electronic cassette 11. The cassette control unit 67 transmits an irradiation start synchronization signal 79 to the electronic cassette 11 in a case where the start of the irradiation of the radiation R is input from the irradiation control unit 66. Furthermore, the cassette control unit 67 transmits an irradiation end synchronization signal 80 to the electronic cassette 11 in a case where the end of the irradiation of the radiation R is input from the irradiation control unit 66. Though not shown, the cassette control unit 67 transmits a gain value and the like of signal charge depending on the irradiation conditions 76 to the electronic cassette 11.

The display-related processing unit 68 displays the radiographic image 20 at an imaging site and executes display-related processing of allowing the operator OP to check a reflected state of the radiographic image 20. The display-related processing unit 68 has an image reception unit 85 and an image processing unit 86. The image reception unit 85 executes reception processing of receiving the radiographic image 20 from the electronic cassette 11 through the communication unit 50. The image reception unit 85 outputs the received radiographic image 20 to the image processing unit 86.

The electronic cassette 11 transmits an image transmission notification signal 87 before the reception of the radiographic image 20. The image transmission notification signal 87 is a signal for informing that the radiographic image 20 is transmitted from now, from the electronic cassette 11 to the mobile radiation generation apparatus 10. The image reception unit 85 receives the image transmission notification signal 87. At a timing at which the image transmission notification signal 87 is received in the image reception unit 85, the display-related processing by the display-related processing unit 68 is started.

The image processing unit 86 executes image processing of processing the radiographic image 20 to a radiographic image for display. Specifically, the image processing unit 86 executes offset correction processing, sensitivity correction processing, defective pixel correction processing, and the like as the image processing. The offset correction processing is processing of subtracting, from the radiographic image 20, an offset correction image detected in a state in which there is no irradiation of the radiation R, in units of pixels. The image processing unit 86 executes the offset correction processing to remove fixed pattern noise due to dark charge or the like from the radiographic image 20. The sensitivity correction processing is processing of correcting variation or the like in sensitivity of each pixel, variation in output characteristic of a circuit that reads the signal charge, and the like based on sensitivity correction data. The defective pixel correction processing is processing of linearly interpolating a pixel value of a defective pixel with a pixel value of a surrounding normal pixel based on information of a defective pixel having an abnormal pixel value generated during shipment, during a periodic inspection, or the like. The offset correction processing, the sensitivity correction processing, and the defective pixel correction processing are processing essential for making the image quality of the radiographic image 20 enough to endure display. The image processing unit 86 outputs the radiographic image 20 subjected to various kinds of image processing to the display control unit 69 and the CAD processing unit 70. At a timing at which the radiographic image 20 is output from the image processing unit 86, the display-related processing by the display-related processing unit 68 is ended.

The CAD processing unit 70 executes CAD processing on the radiographic image 20. The CAD processing is, for example, processing of extracting a candidate of a lesion, such as a tumor, reflected in the radiographic image 20. The CAD processing unit 70 outputs a result of the CAD processing to the display control unit 69. In this way, the CPU 53 that is one processor executes both the display-related processing and the CAD processing.

As shown in FIG. 3, the display control unit 69 performs control such that the radiographic image 20 is displayed on the display 32. The display control unit 69 performs controls such that the result of the CAD processing is displayed on the display 32 (see FIG. 15).

The main control unit 71 controls the operations of the irradiation control unit 66, the cassette control unit 67, the display-related processing unit 68, the display control unit 69, and the CAD processing unit 70. For example, in a case where the display-related processing by the display-related processing unit 68 and the CAD processing by the CAD processing unit 70 compete with each other, the main control unit 71 executes priority processing of giving priority to the display-related processing over the CAD processing. That is, the main control unit 71 is an example of a "priority processing unit" according to the technique of the present disclosure.

The main control unit 71 also controls the operation of a cooling fan 56. In more detail, the main control unit 71 increases and decreases a rotation speed of the cooling fan 56, thereby setting a cooling level of the cooling fan 56 high and low.

Figures 6, 7:
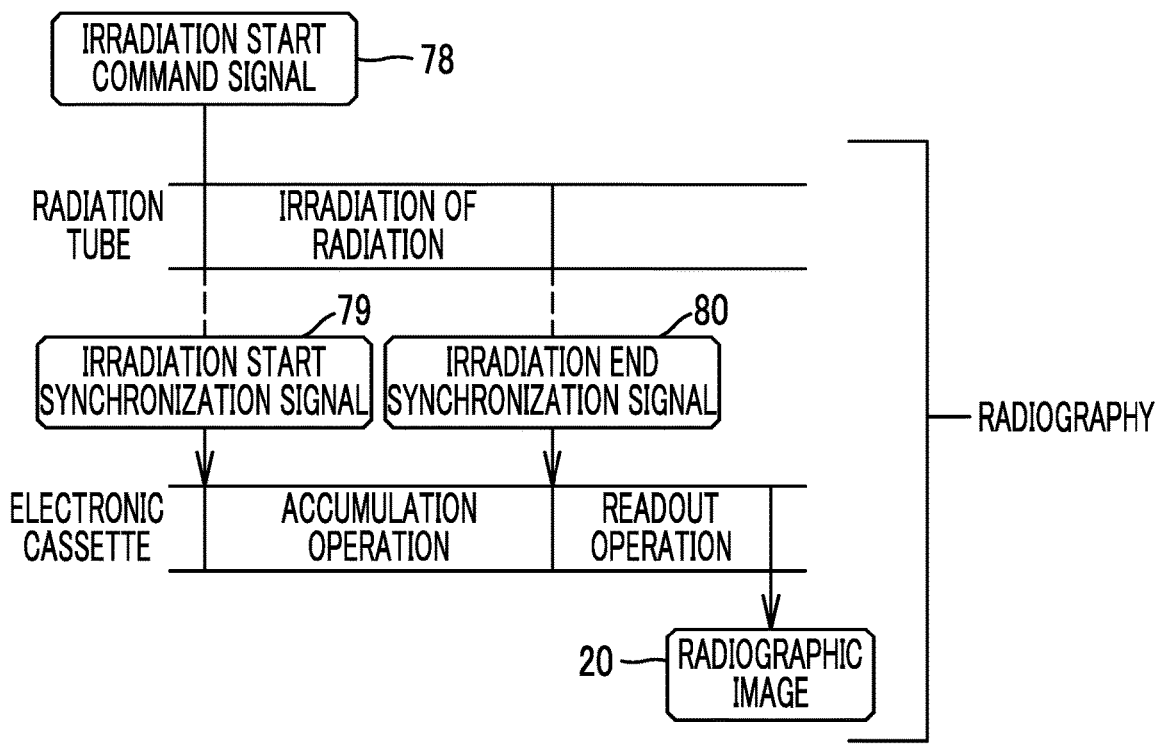
FIG. 6 is a diagram showing an irradiation condition table.
FIG. 7 is a diagram showing radiography.

As shown in FIG. 6, in the irradiation condition table 61, the irradiation conditions 76 corresponding to various imaging menus 75 are registered. The imaging menu 75 defines an imaging procedure having a set of an imaging part, a posture, and an imaging direction, such as "front chest decubitus". The imaging part is a head, a neck, an abdomen, a waist, a shoulder, an elbow, a hand, a knee, an ankle, and the like in addition to the chest. The posture is an upright posture, a sitting posture, and the like in addition to the decubitus posture. The imaging direction is a rear surface, a lateral surface, and the like in addition to the front surface. Information regarding a body shape of the subject H, such as "body shape small", is also included in the imaging menu 75. As described above, the irradiation condition 76 is a set of a tube voltage, a tube current, and an irradiation time. Instead of the tube current and the irradiation time, a tube current and irradiation time product may be set as the irradiation condition 76.

The mobile radiation generation apparatus 10 receives an imaging order from the RIS through the communication unit 50. In the imaging order, identification data (ID) for identifying the subject H, instruction information of an imaging procedure by a treatment department physician or the like who issues the imaging order, and the like are registered. The mobile radiation generation apparatus 10 displays the imaging order from the RIS on the display 32 according to an operation of the operator OP. The operator OP confirms the content of the imaging order through the display 32.

The mobile radiation generation apparatus 10 displays one of a plurality of electronic cassettes 11 stored in the cassette storage portion 30 on the display 32 in a selectable form. The operator OP selects one electronic cassette 11 that is used to image the subject H indicated by the imaging order. With this, the selected electronic cassette 11 and the imaging order are associated with each other.

The mobile radiation generation apparatus 10 displays the imaging menu 75 on the display 32 in a selectable form. The operator OP selects the imaging menu 75 that coincides with the imaging procedure designated by the imaging order and coincides with the body shape of the subject H. With this, the imaging menu 75 is received by the reception unit 65, and the irradiation conditions 76 corresponding to the imaging menu 75 are read out from the irradiation condition table 61 to the reception unit 65. As a result, the irradiation conditions 76 are set in the voltage generator 48 by the irradiation control unit 66. The irradiation conditions 76 read out from the irradiation condition table 61 can be finely adjusted by the operator OP through the operation panel 33 before being set in the voltage generator 48.

As shown in FIG. 7, the radiation tube 47 generates the radiation R in conformity with the irradiation start instruction signal 78 from the irradiation switch 34. The electronic cassette 11 performs an accumulation operation to make the pixels accumulate the signal charge according to the irradiation start synchronization signal 79 transmitted in conformity with the irradiation start timing of the radiation R after performing a reset operation (not shown) to read out and discard dark charge from the pixels of the sensor panel. The electronic cassette 11 performs a readout operation to read out the signal charge accumulated in the pixels and to output the signal charge as the radiographic image 20 according to the irradiation end synchronization signal 80 transmitted in conformity with the irradiation end timing of the radiation R. The series of operations to cause the irradiation of the radiation R from the radiation tube 47 and to output the radiographic image 20 from the electronic cassette 11 is defined as "radiography" according to the technique of the present disclosure.

Figure 8:
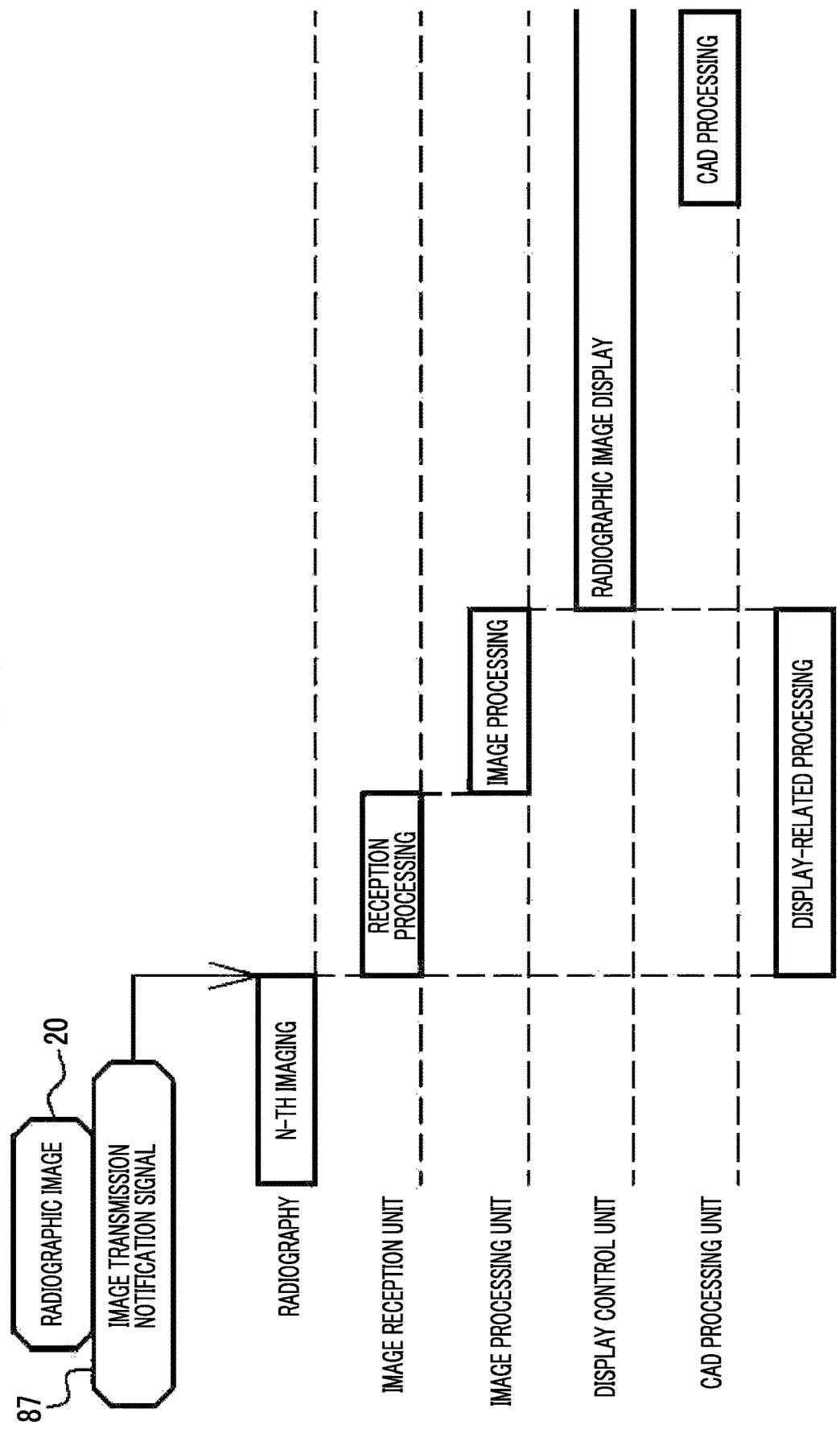
FIG. 8 is a diagram showing a flow of display-related processing and CAD processing on N-th imaging.

As shown in FIG. 8, in a case where a set time has elapsed after display-related processing on N-th (where N is a natural number equal to or greater than one) radiography (hereinafter, referred to as N-th imaging) is ended in the display-related processing unit 68, and the radiographic image 20 is displayed on the display 32, the main control unit 71 makes the CAD processing unit 70 automatically start CAD processing on N-th imaging. The set time is, for example, one minute. The N-th imaging is an example of "present imaging" and "first imaging" according to the technique of the present disclosure.

Figure 9:
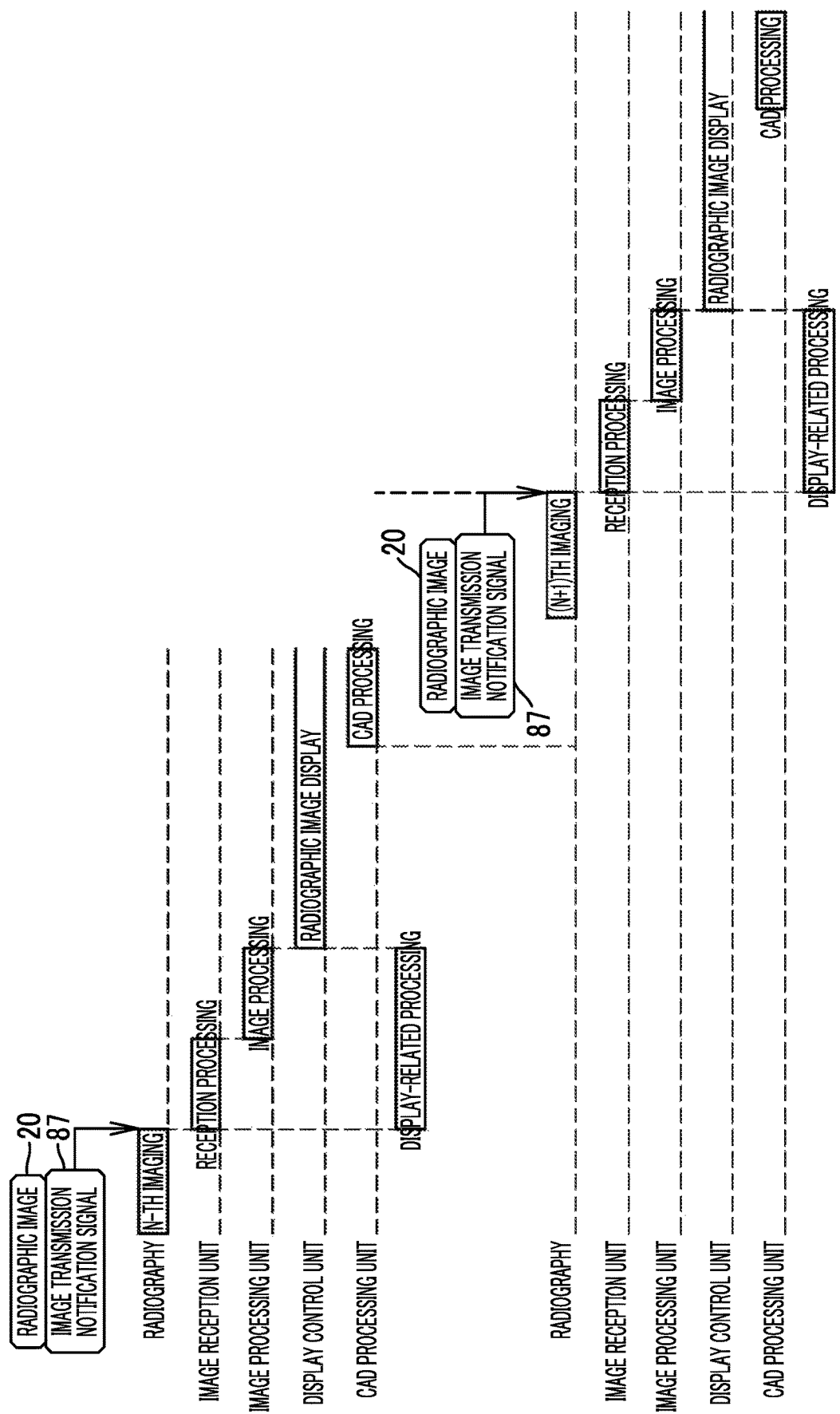
FIG. 9 is a diagram showing a case where (N+1)th imaging is performed after the CAD processing on the N-th imaging is ended, and display-related processing on (N+1)th imaging is started.

FIG. 9 shows a case where (N+1)th radiography (hereinafter, referred to as (N+1)th imaging) is performed after the CAD processing on the N-th imaging is ended, and the display-related processing on the (N+1)th imaging is started. In this case, since the CAD processing on the N-th imaging and the display-related processing on the (N+1)th imaging do not compete with each other, the main control unit 71 does not execute the priority processing of giving priority to the display-related processing over the CAD processing. The (N+1)th imaging is an example of "next imaging" and "second imaging" according to the technique of the present disclosure.

Figure 10:
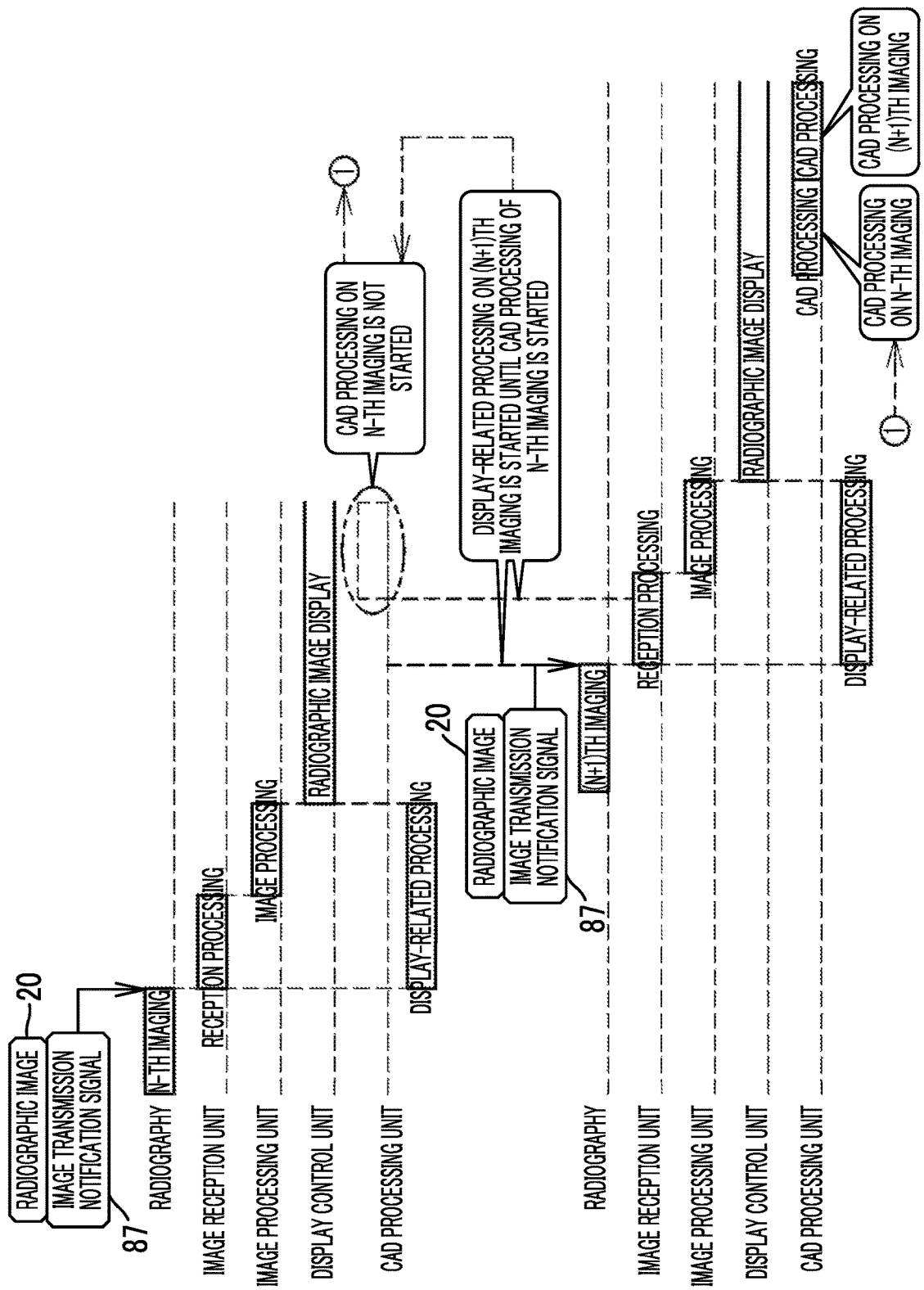
FIG. 10 is a diagram showing a case where, in a period from when the display-related processing on the N-th imaging is ended to when the CAD processing on the N-th imaging is started, (N+1)th imaging is performed, and the display-related processing on the (N+1)th imaging is started.

FIG. 10 shows a case where, in a period from when the display-related processing on the N-th imaging is ended to when the CAD processing on the N-th imaging is started, the (N+1)th imaging is performed, and the display-related processing on the (N+1)th imaging is started. In this case, in a case where the CAD processing on the N-th imaging is started without change, since the CAD processing on the N-th imaging competes with the display-related processing on the (N+1)th imaging, the main control unit 71 does not start the CAD processing on the N-th imaging. That is, while the display-related processing is being executed, the main control unit 71 prohibits the execution of the CAD processing as the priority processing.

In a case where the set time has elapsed after the display-related processing on the (N+1)th imaging is ended, the main control unit 71 makes the CAD processing unit 70 execute the CAD processing on the N-th imaging of which the start is postponed. The main control unit 71 subsequently makes the CAD processing unit 70 execute the CAD processing on the (N+1)th imaging after the CAD processing on the N-th imaging is ended. In a period from when the display-related processing on the (N+1)th imaging is ended to when the CAD processing on the N-th imaging is started, in a case where (N+2)th imaging is performed, and the display-related processing on the (N+2)th imaging is started, the CAD processing on the N-th imaging and the CAD processing on the (N+1)th imaging are not executed, and are carried over after the end of the display-related processing on the (N+2)th imaging.

Figure 11:
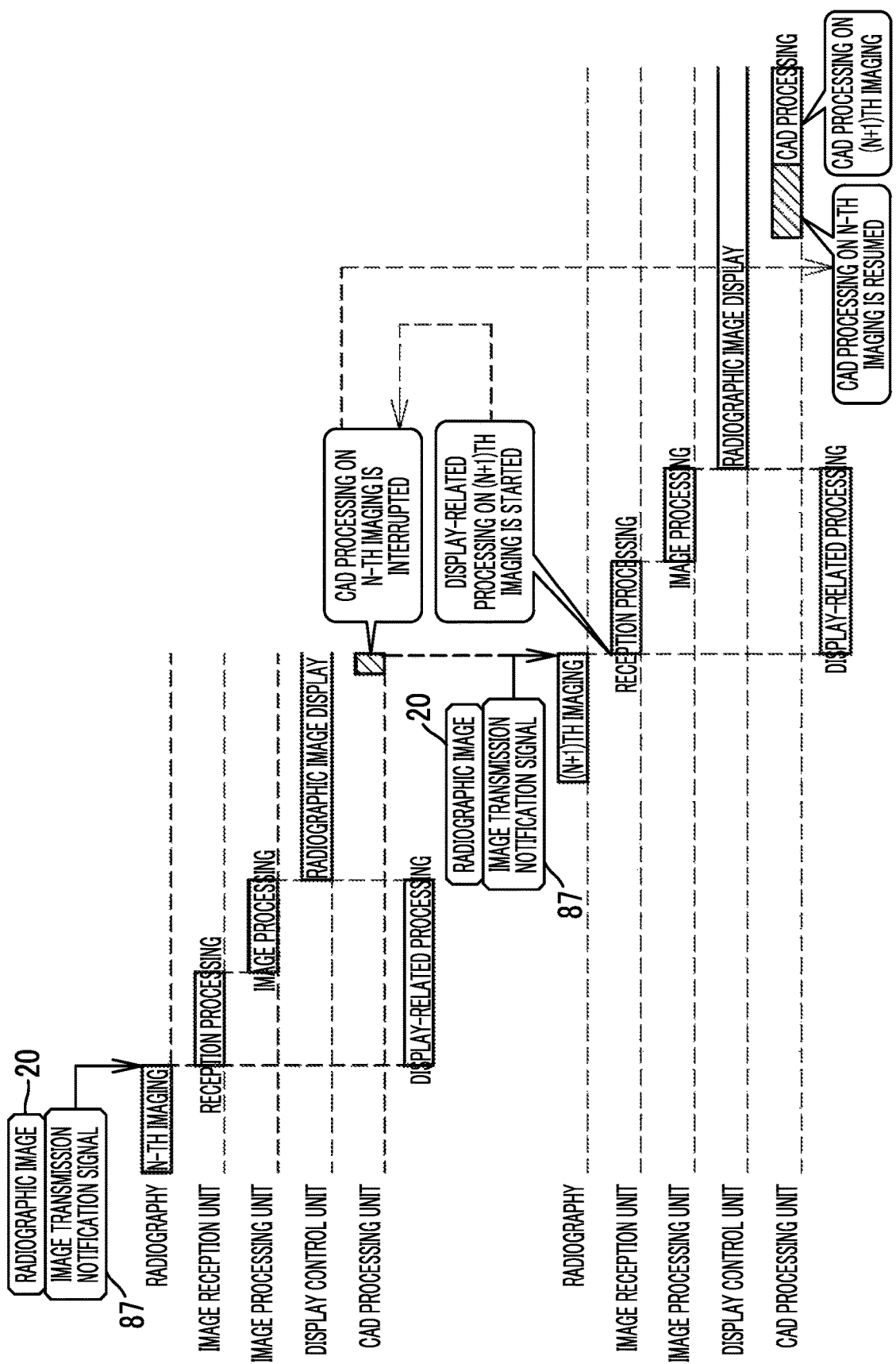
FIG. 11 is a diagram showing a case where, while the CAD processing on the N-th imaging is being executed, the (N+1)th imaging is performed, and the display-related processing on the (N+1)th imaging is started.

FIG. 11 shows a case where the (N+1)th imaging is performed while the CAD processing on the N-th imaging is being executed. In this case, since the CAD processing on the N-th imaging and the display-related processing on the (N+1)th imaging compete with each other, the main control unit 71 interrupts the CAD processing on the N-th imaging and starts the display-related processing on the (N+1)th imaging, as the priority processing. The CAD processing unit 70 temporarily stores intermediate data in the middle of the CAD processing in the memory 52.

In a case where the set time has elapsed after the display-related processing on the (N+1)th imaging is ended, the main control unit 71 makes the CAD processing unit 70 automatically resume the interrupted CAD processing on the N-th imaging. In this case, the CAD processing unit 70 reads out the intermediate data temporarily stored in the memory 52 from the memory 52. The main control unit 71 subsequently makes the CAD processing unit 70 execute the CAD processing on the (N+1)th imaging after the CAD processing on the N-th imaging is ended.

Figure 12:
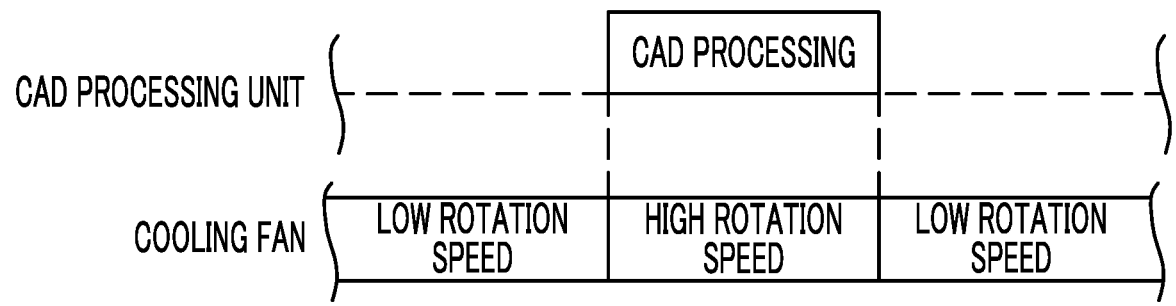
FIG. 12 is a diagram showing a relationship between the CAD processing and a rotation speed of a cooling fan.

As shown in FIG. 12, the main control unit 71 increases the rotation speed of the cooling fan 56 compared to a case where the CAD processing is not executed. With this, the main control unit 71 sets the cooling level of the cooling fan 56 in a case where the CAD processing is being executed higher than a normal state.

Figure 13:
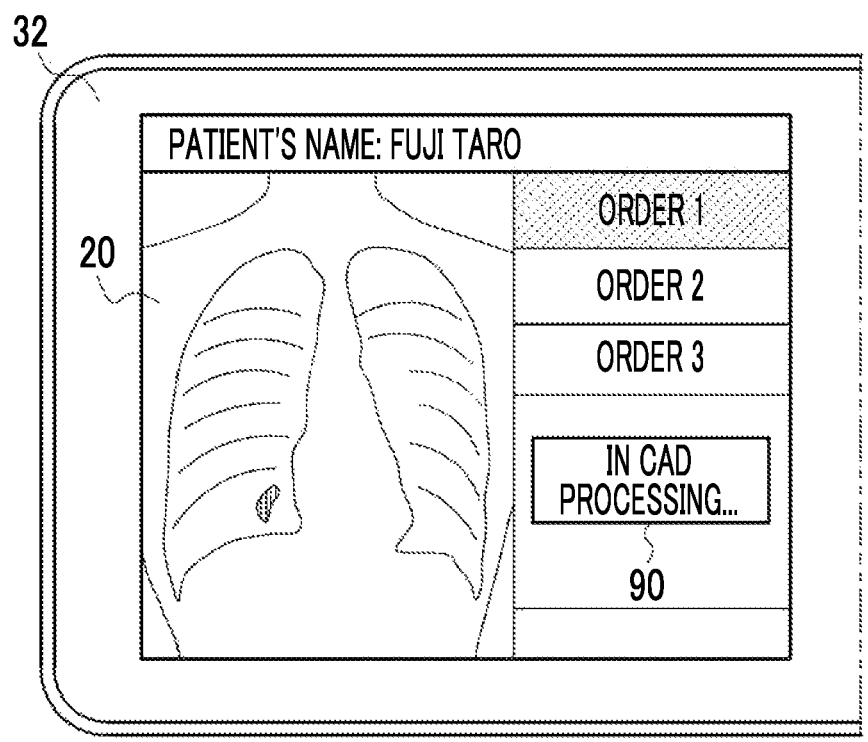
FIG. 13 is a diagram showing a state in which a message box indicating that the CAD processing is being executed is displayed.

While the CAD processing is being executed in the CAD processing unit 70, as shown in FIG. 13, the display control unit 69 displays a message box 90 indicating that the CAD processing is being executed, on the display 32.

Figure 14:
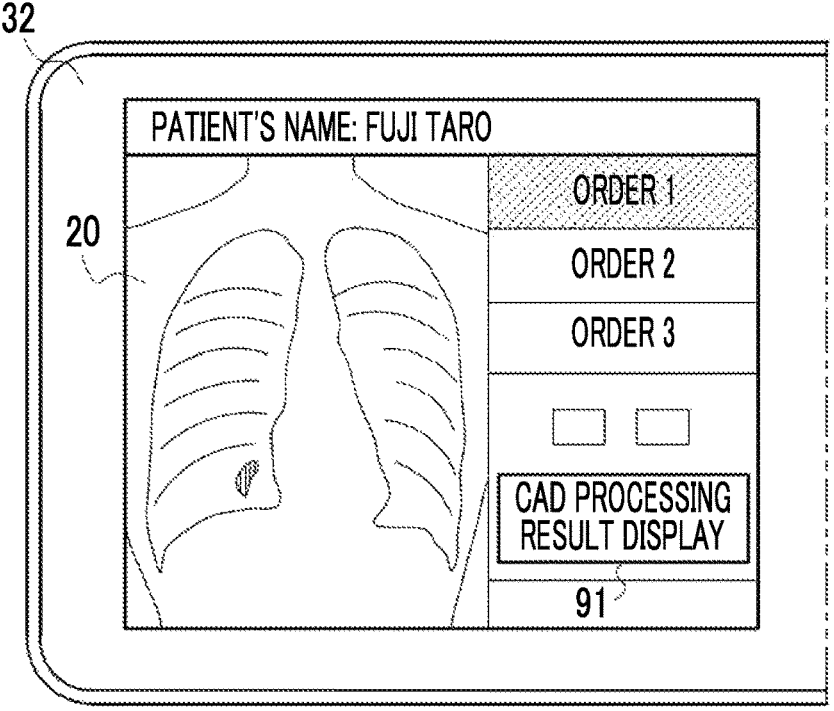
FIG. 14 is a diagram showing a state in which a CAD processing result display button is displayed.
Figure 15:
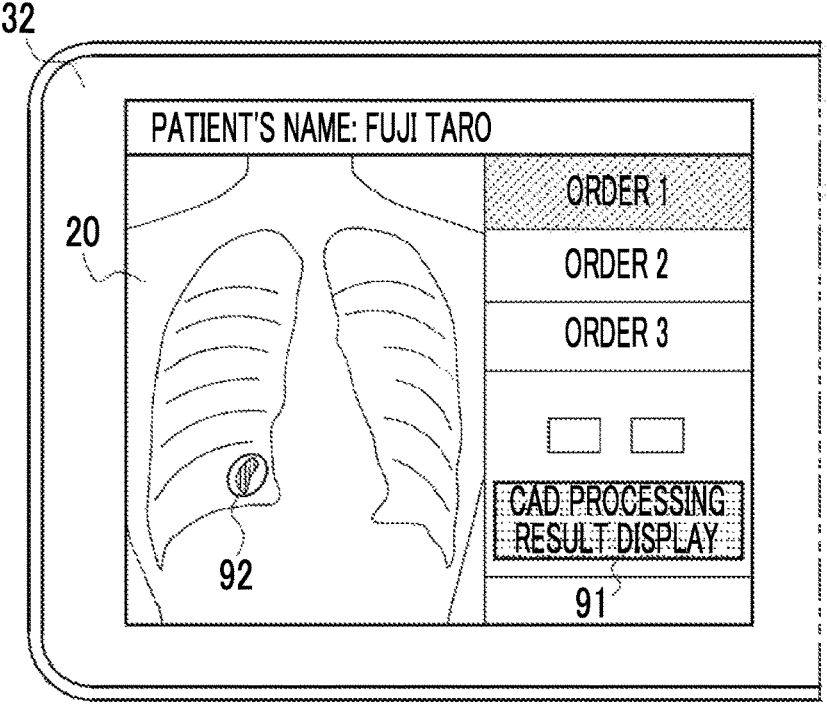
FIG. 15 is a diagram showing a state in which a result of the CAD processing is displayed.

In a case where the CAD processing is ended, as shown in FIG. 14, the display control unit 69 displays a CAD processing result display button 91 for displaying the result of the CAD processing, on the display 32. In a case where the CAD processing result display button 91 is selected by the operator OP, as shown in FIG. 15, the display control unit 69 displays a marker 92 surrounding a candidate of a lesion extracted by the CAD processing as the result of the CAD processing on the radiographic image 20.

Figure 16:
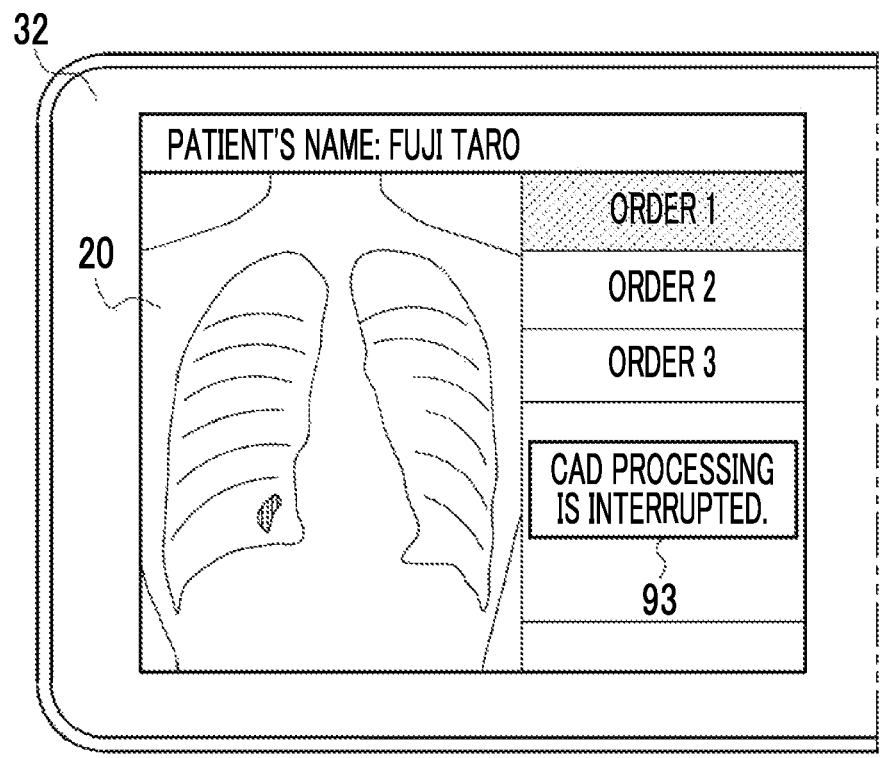
FIG. 16 is a diagram showing a state in which a message box indicating that the CAD processing is interrupted is displayed.

As shown in FIG. 11, in a case where the CAD processing is interrupted by the main control unit 71, as shown in FIG. 16, the display control unit 69 displays a message box 93 indicating that the CAD processing is interrupted, on the display 32.

In regard to the radiographic image 20 and the result of the CAD processing on radiography of each time, display can be switched by selection of "order 1", "order 2", and the like on the right side of the radiographic image 20. For example, in a case of displaying the radiographic image 20 and the result of the CAD processing on the first imaging, "order 1" on the first imaging is selected as shown in FIG. 13 and the like. Then, in a case of displaying the radiographic image 20 and the result of the CAD processing on the second imaging, "order 2" on the second imaging is selected.

Next, the operations of the above-described configuration will be described referring to flowcharts of FIGS. 17 and 18. In a case where the operation program 60 is activated, as shown in FIG. 5, the CPU 53 of the console 55 functions as the reception unit 65, the irradiation control unit 66, the cassette control unit 67, the display-related processing unit 68, the display control unit 69, the CAD processing unit 70, and the main control unit 71.

Before the N-th imaging, the imaging menu 75 corresponding to the imaging order is selected by the operator OP through the display 32, and the imaging menu 75 is received in the reception unit 65. Then, the irradiation conditions 76 corresponding to the imaging menu 75 are read out from the irradiation condition table 61 by the reception unit 65. The read-out irradiation conditions 76 are finely adjusted by the operator OP as needed and are set in the voltage generator 48 by the irradiation control unit 66.

After the irradiation conditions 76 are set, the irradiation switch 34 is operated by the operator OP, and the warm-up instruction signal 77 and the irradiation start instruction signal 78 are received in the reception unit 65. With this, as shown in FIG. 7, the irradiation of the radiation R from the radiation tube 47 is performed under the set irradiation conditions 76. In the electronic cassette 11, the accumulation operation is performed in response to the irradiation start synchronization signal 79, and the readout operation is performed in response to the irradiation end synchronization signal 80. With this, the radiographic image 20 is output from the electronic cassette 11.

Figure 17:
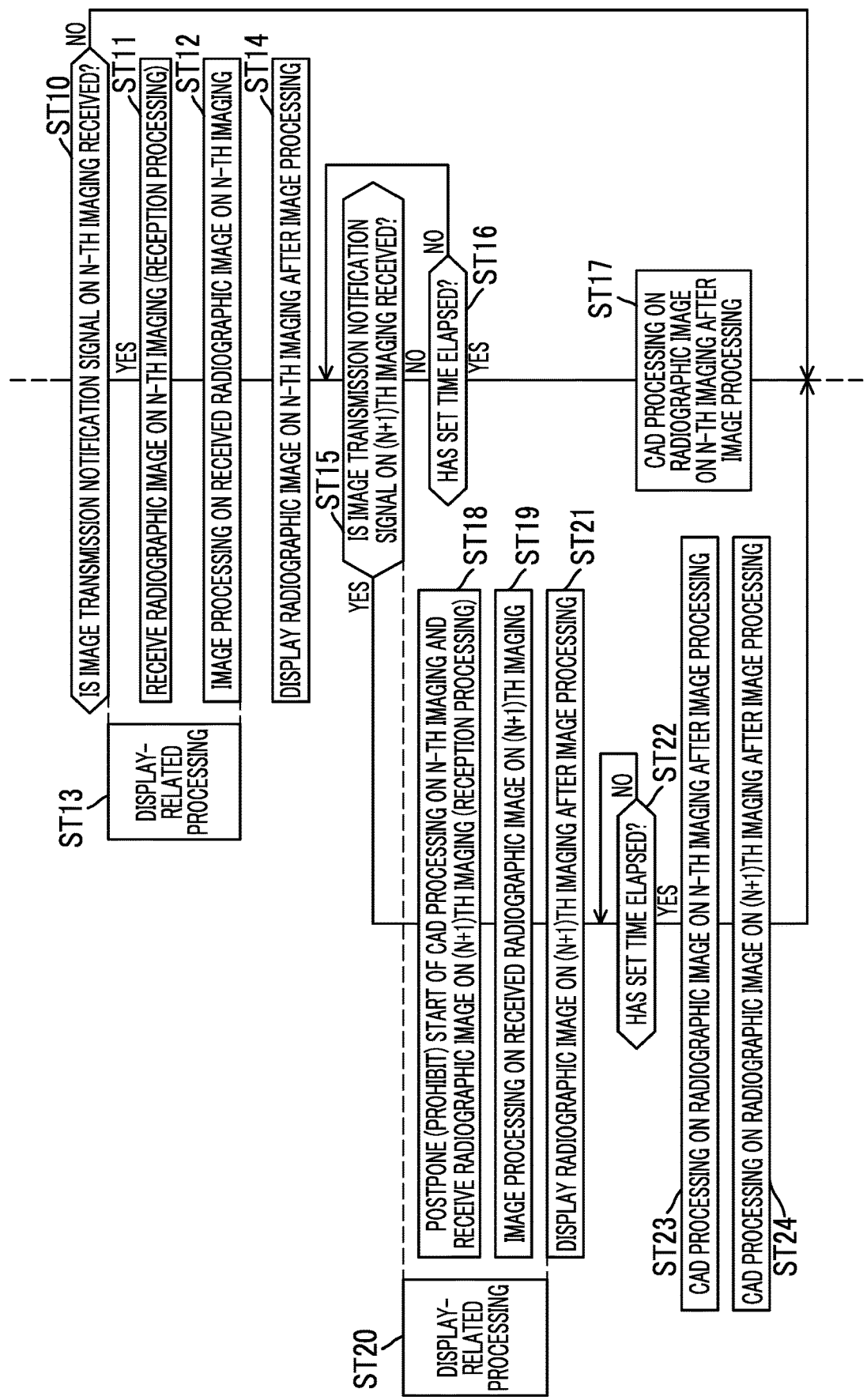
FIG. 17 is a flowchart illustrating an aspect shown in FIGS. 9 and 10.

FIG. 17 is a flowchart illustrating the aspect shown in FIGS. 9 and 10. First, the N-th imaging is performed, the radiographic image 20 on the N-th imaging is output from the electronic cassette 11, in a case where the image transmission notification signal 87 on the N-th imaging is received in the image reception unit 85 (in Step ST10, YES), and subsequently, the radiographic image 20 on the N-th imaging is received in the image reception unit 85 (Step ST11). The radiographic image 20 on the N-th imaging is output from the image reception unit 85 to the image processing unit 86.

In the image processing unit 86, various kinds of image processing, such as offset correction processing, sensitivity correction processing, and defective pixel correction processing, are executed on the radiographic image 20 on the N-th imaging (Step ST12). The radiographic image 20 on the N-th imaging after the image processing is output from the image processing unit 86 to the display control unit 69 and the CAD processing unit 70.

As shown in Step ST13, the display-related processing on the N-th imaging is started at a timing at which the image transmission notification signal 87 on the N-th imaging is received in the image reception unit 85. Then, the display-related processing on the N-th imaging is ended at a timing at which the radiographic image 20 on the N-th imaging after the image processing is output from the image processing unit 86. Step ST13 is an example of a "display-related processing step" according to the technique of the present disclosure.

As shown in FIG. 3, the radiographic image 20 on the N-th imaging after the image processing is displayed on the display 32 by the display control unit 69 (Step ST14). With this, the operator OP can instantly check a reflected state of the radiographic image 20 obtained through the N-th imaging at an imaging site.

In a period from when the display-related processing on the N-th imaging is ended in the display-related processing unit 68 to when the set time elapses, in a case where the (N+1)th imaging is not performed, and the image transmission notification signal 87 on the (N+1)th imaging is not received in the image reception unit 85 (in Step ST15, NO and in Step ST16, YES), the CAD processing is executed on the radiographic image 20 on the N-th imaging after the image processing by the CAD processing unit 70 (Step ST17). Step ST17 is an example of a "computer aided diagnosis processing step" according to the technique of the present disclosure.

While the CAD processing is being executed, as shown in FIG. 12, the cooling level of the cooling fan 56 is set higher than the normal state under the control of the main control unit 71. As shown in FIG. 13, to inform the operator OP that the CAD processing is being executed, the message box 90 is displayed by the display control unit 69. The result of the CAD processing is output from the CAD processing unit 70 to the display control unit 69. The result of the CAD processing is displayed on the display 32 by the display control unit 69 as shown in FIG. 15 in a case where the CAD processing result display button 91 is selected.

On the other hand, in a period from when the display-related processing on the N-th imaging is ended in the display-related processing unit 68 to when the set time elapses, in a case where the (N+1)th imaging is performed, and the image transmission notification signal 87 on the (N+1)th imaging is received in the image reception unit 85 (in Step ST15, YES), the start of the CAD processing on the N-th imaging is postponed, and the CAD processing is prohibited. Then, the radiographic image 20 on the (N+1)th imaging is received in the image reception unit 85 (Step ST18). The radiographic image 20 on the (N+1)th imaging is output from the image reception unit 85 to the image processing unit 86. Step ST18 is an example of a "priority processing step" according to the technique of the present disclosure.

In the image processing unit 86, the image processing is executed on the radiographic image 20 on the (N+1)th imaging (Step ST19). The radiographic image 20 on the (N+1)th imaging after the image processing is output from the image processing unit 86 to the display control unit 69 and the CAD processing unit 70.

As shown in Step ST20, the display-related processing on the (N+1)th imaging is started at a timing at which the image transmission notification signal 87 on the (N+1)th imaging is received in the image reception unit 85. Then, the display-related processing on the (N+1)th imaging is ended at a timing at which the radiographic image 20 on the (N+1)th imaging after the image processing is output from the image processing unit 86. Like Step ST13, Step ST20 is an example of a "display-related processing step" according to the technique of the present disclosure.

The radiographic image 20 on the (N+1)th imaging after the image processing is displayed on the display 32 by the display control unit 69 (Step ST21).

In a case where the set time has elapsed after the display-related processing on (N+1)th imaging is ended in the display-related processing unit 68 (in Step ST22, YES), the CAD processing is executed on the radiographic image 20 on the N-th imaging of which the start is postponed in Step ST18, by the CAD processing unit 70 (Step ST23). The CAD processing on the (N+1)th imaging is subsequently executed (Step ST24). Like Step ST17, Steps ST23 and ST24 are an example of a "computer aided diagnosis processing step" according to the technique of the present disclosure.

Figure 18:
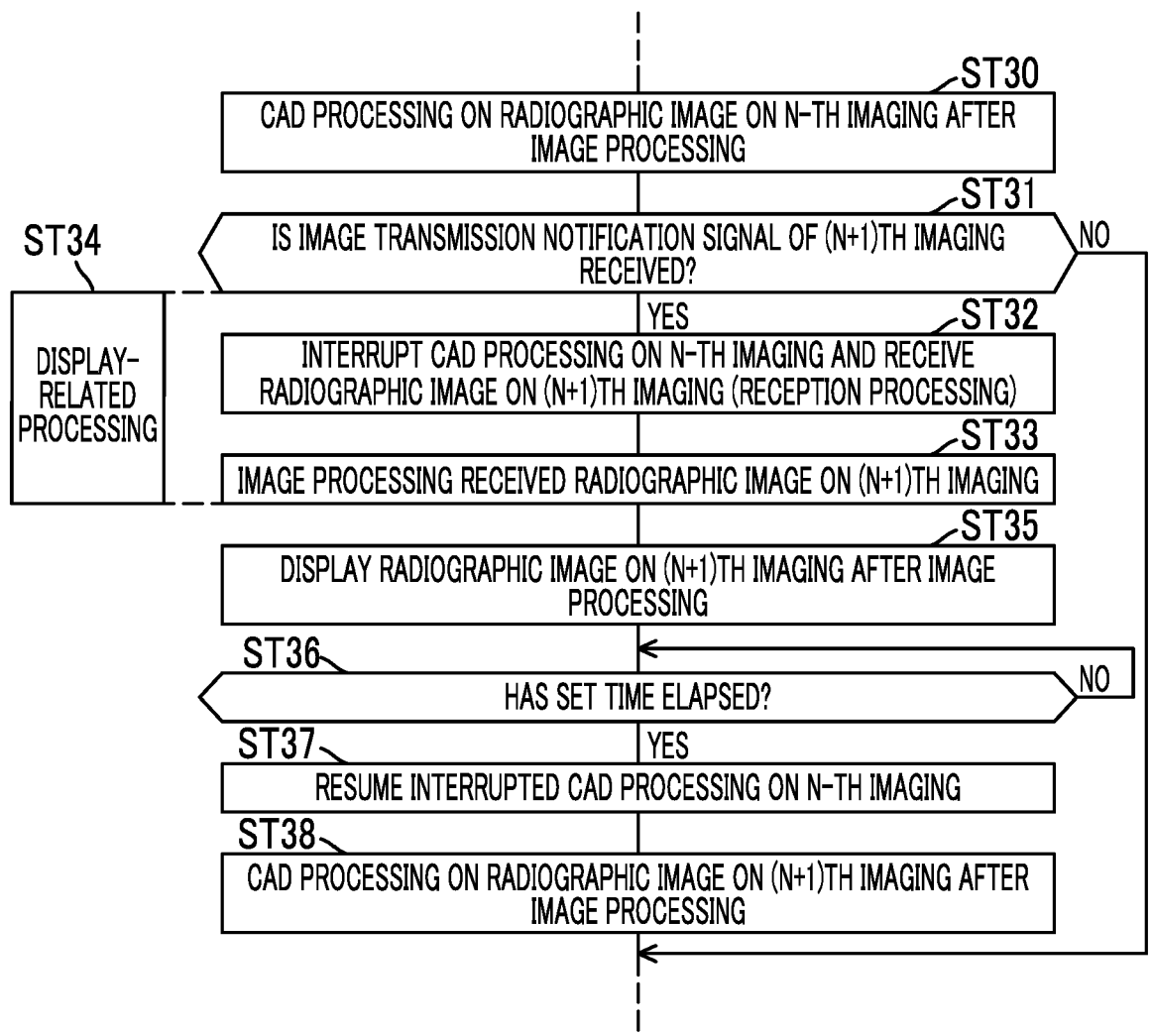
FIG. 18 is a flowchart illustrating an aspect shown in FIG. 11.

FIG. 18 is a flowchart illustrating the aspect shown in FIG. 11. First, the CAD processing is executed on the radiographic image 20 on the N-th imaging after the image processing by the CAD processing unit 70 (Step ST30). Like Steps ST17, ST23, and ST24, Step ST30 is an example of a "computer aided diagnosis processing step" according to the technique of the present disclosure.

While the CAD processing on the N-th imaging is being executed, in a case where the (N+1)th imaging is performed and the image transmission notification signal 87 on the (N+1)th imaging is received in the image reception unit 85 (in Step ST31, YES), the CAD processing on the N-th imaging is interrupted. Then, the radiographic image 20 on the (N+1)th imaging is received in the image reception unit 85 (Step ST32). The radiographic image 20 on the (N+1)th imaging is output from the image reception unit 85 to the image processing unit 86. Like Step ST18, Step ST32 is an example of a "priority processing step" according to the technique of the present disclosure.

In a case where the CAD processing on the N-th imaging is interrupted, as shown in FIG. 16, the message box 93 is displayed by the display control unit 69.

In the image processing unit 86, the image processing is executed on the radiographic image 20 on the (N+1)th imaging (Step ST33). The radiographic image 20 on the (N+1)th imaging after the image processing is output from the image processing unit 86 to the display control unit 69 and the CAD processing unit 70.

As shown in Step ST34, the display-related processing on the (N+1)th imaging is started at a timing at which the image transmission notification signal 87 on the (N+1)th imaging is received in the image reception unit 85. Then, the display-related processing on the (N+1)th imaging is ended at a timing at which the radiographic image 20 on the (N+1)th imaging after the image processing is output from the image processing unit 86. Like Steps ST13 and ST20, Step ST34 is an example of a "display-related processing step" according to the technique of the present disclosure.

The radiographic image 20 on the (N+1)th imaging after the image processing is displayed on the display 32 by the display control unit 69 (Step ST35).

In a case where the set time has elapsed after the display-related processing on the (N+1)th imaging is ended in the display-related processing unit 68 (in Step ST36, YES), the interrupted CAD processing on the N-th imaging is automatically resumed by the CAD processing unit 70 (Step ST37). After the CAD processing on the N-th imaging is ended, the CAD processing on the (N+1)th imaging is subsequently executed (Step ST38). Like Steps ST17, ST23, ST24, and ST30, Steps ST37 and ST38 are an example of a "computer aided diagnosis processing step" according to the technique of the present disclosure.

As described above, the CPU 53 of the console 55 comprises the display-related processing unit 68, the CAD processing unit 70, and the main control unit 71. The display-related processing unit 68 executes the display-related processing of displaying, at the imaging site, the radiographic image 20 obtained by radiography. The display-related processing includes the reception processing of receiving the radiographic image 20 from the electronic cassette 11 and the image processing of processing the received radiographic image 20 to the radiographic image for display. The CAD processing unit 70 executes the CAD processing on the radiographic image 20 after the image processing. In a case where the display-related processing and the CAD processing compete with each other, the main control unit 71 executes the priority processing of giving priority to the display-related processing over the CAD processing. For this reason, it is possible to reduce a concern that the display-related processing is delayed due to the CAD processing having a comparatively large processing load, and the display of the radiographic image 20 is hindered. Accordingly, it is possible to allow the operator OP to check the reflected state of the radiographic image 20 without hindrance.

The main control unit 71 prohibits the execution of the CAD processing while the display-related processing is being executed, as the priority processing. Specifically, the main control unit 71 does not start the CAD processing on the N-th imaging in a case where the display-related processing on the (N+1)th imaging starts in a period from when the display-related processing on the N-th imaging ends to when the CAD processing on the N-th imaging automatically starts subsequently. The main control unit 71 interrupts the CAD processing on the N-th imaging and starts the display-related processing on the (N+1)th imaging after the N-th imaging, as the priority processing. For this reason, it is possible to eliminate a concern that the display-related processing is delayed due to the CAD processing, and the display of the radiographic image 20 is hindered.

The CAD processing unit 70 automatically resumes the interrupted CAD processing on the N-th imaging after the display-related processing on the (N+1)th imaging ends. For this reason, even in a case where the CAD processing on the N-th imaging is interrupted, it is possible to obtain the result of the CAD processing on the N-th imaging without bothering the operator OP.

The display control unit 69 displays the message box 93, thereby notifying the operator OP that the CAD processing on the N-th imaging is interrupted. For this reason, it is possible to allow the operator OP to reliably know that the CAD processing on the N-th imaging is interrupted.

The processor that executes the display-related processing and the CAD processing is one CPU 53. For this reason, the display-related processing is highly likely to be delayed due to the CAD processing. Accordingly, it is possible to further exhibit the effect of the priority processing.

The display-related processing unit 68 starts the display-related processing at a timing at which the image transmission notification signal 87 is received in the image reception unit 85, that is, a start timing of the reception processing. For this reason, while the imaging menu 75 is received and the irradiation conditions 76 are being set or the irradiation switch 34 is operated and the irradiation of the radiation R is being performed, the CAD processing can be executed.

While the CAD processing is being executed, the main control unit 71 sets the cooling level of the cooling fan 56 higher than the normal state. For this reason, it is possible to efficiently cool the CPU 53 that generates heat with an increase in processing load due to the CAD processing. It is possible to suppress degradation of throughput of the CPU 53 due to heat generation.

The console 55 is mounted in the mobile radiation generation apparatus 10 that has the radiation generation unit 15 that emits the radiation R and is driven with the battery 58 in a wireless manner. The console 55 that is mounted in the mobile radiation generation apparatus 10 has limited resources of a processor, such as the CPU 53, compared to a console that is connected to a radiation generation apparatus installed at an imaging stand. For this reason, the display-related processing is more highly likely to be delayed due to the CAD processing. Accordingly, the technique of the present disclosure is applied to the console 55 that is mounted in the mobile radiation generation apparatus 10, whereby it is possible to further exhibit the effect of the priority processing.

Second Embodiment

In the first embodiment described above, although the CAD processing automatically starts, the technique of the present disclosure is not limited thereto. As in a second embodiment shown in FIGS. 19 to 22, in a case where there is an execution instruction of the CAD processing from the operator OP, the CAD processing may be executed.

Figure 19:
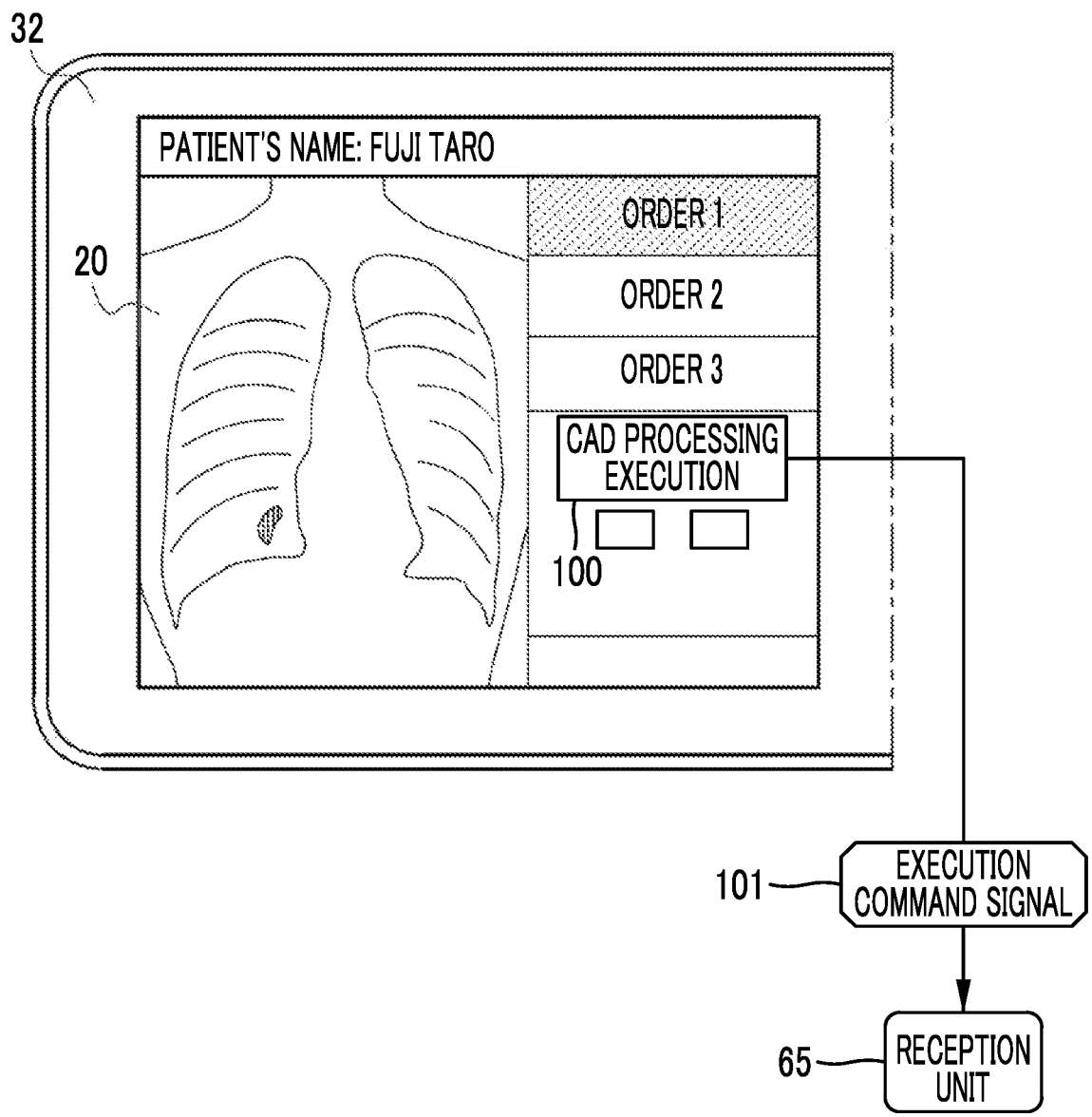
FIG. 19 is a diagram showing a second embodiment in which an execution instruction of CAD processing from an operator is received.

As shown in FIG. 19, the display control unit 69 displays a CAD processing execution button 100 for inputting the execution instruction of the CAD processing on the display 32. The operator OP selects the CAD processing execution button 100 in a case where the operator OP wants to execute the CAD processing on the displayed radiographic image 20. In a case where the CAD processing execution button 100 is selected by the operator OP, an execution instruction signal 101 that instructs the execution of the CAD processing is sent from the display 32 and is received in the reception unit 65. With this, the CAD processing is executed in the CAD processing unit 70.

Figure 20:
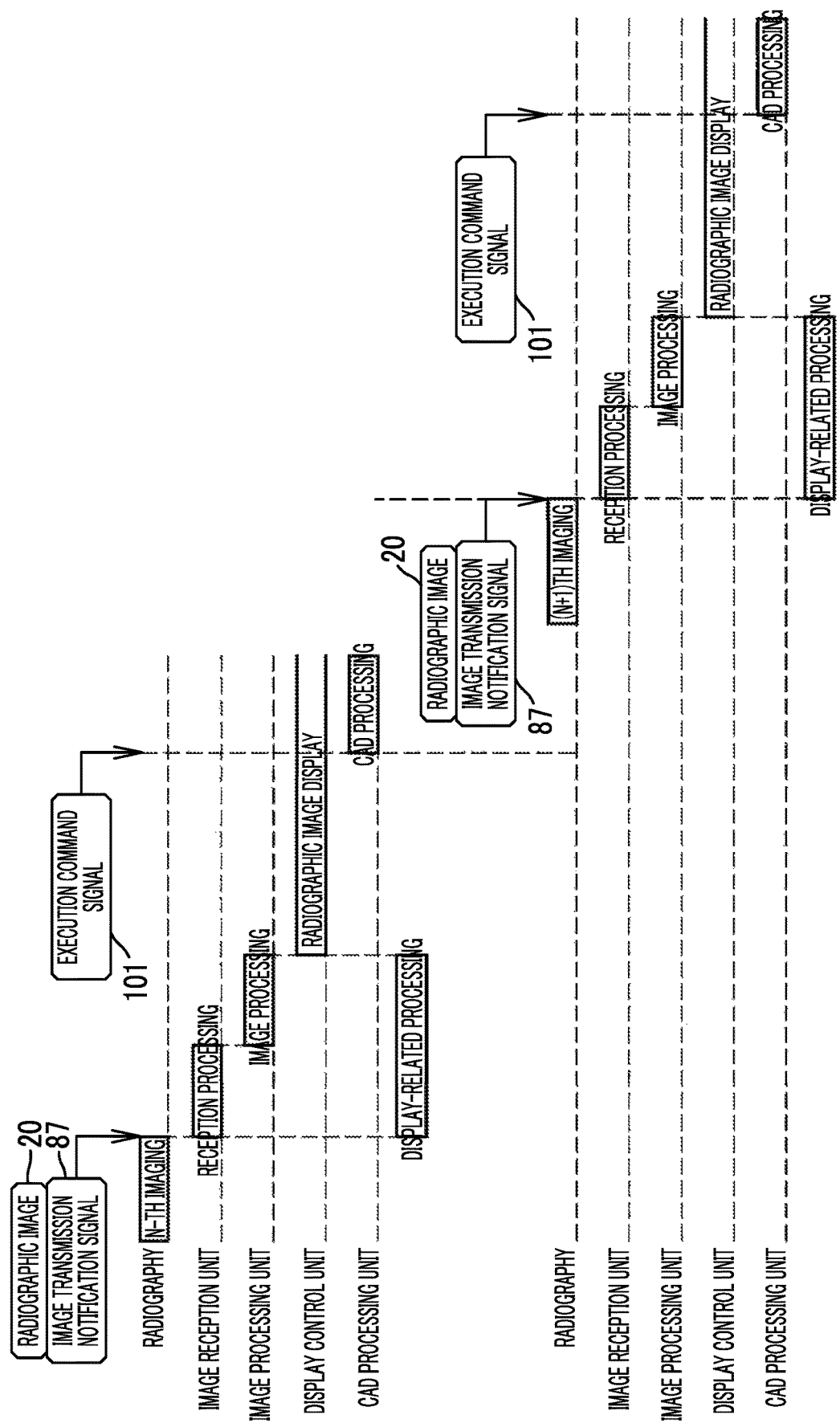
FIG. 20 is a diagram showing a case where CAD processing on N-th imaging is executed in response to an execution instruction signal, (N+1)th imaging is performed after the CAD processing on the N-th imaging is ended, and display-related processing on the (N+1)th imaging is started.

FIG. 20 shows a case where the CAD processing on the N-th imaging is executed in response to the execution instruction signal 101, the (N+1)th imaging is performed after the CAD processing on the N-th imaging is ended, and the display-related processing on the (N+1)th imaging is started. In this case, as in the case of FIG. 9, since the CAD processing on the N-th imaging and the display-related processing on the (N+1)th imaging do not compete with each other, the main control unit 71 does not execute the priority processing.

Figure 21:
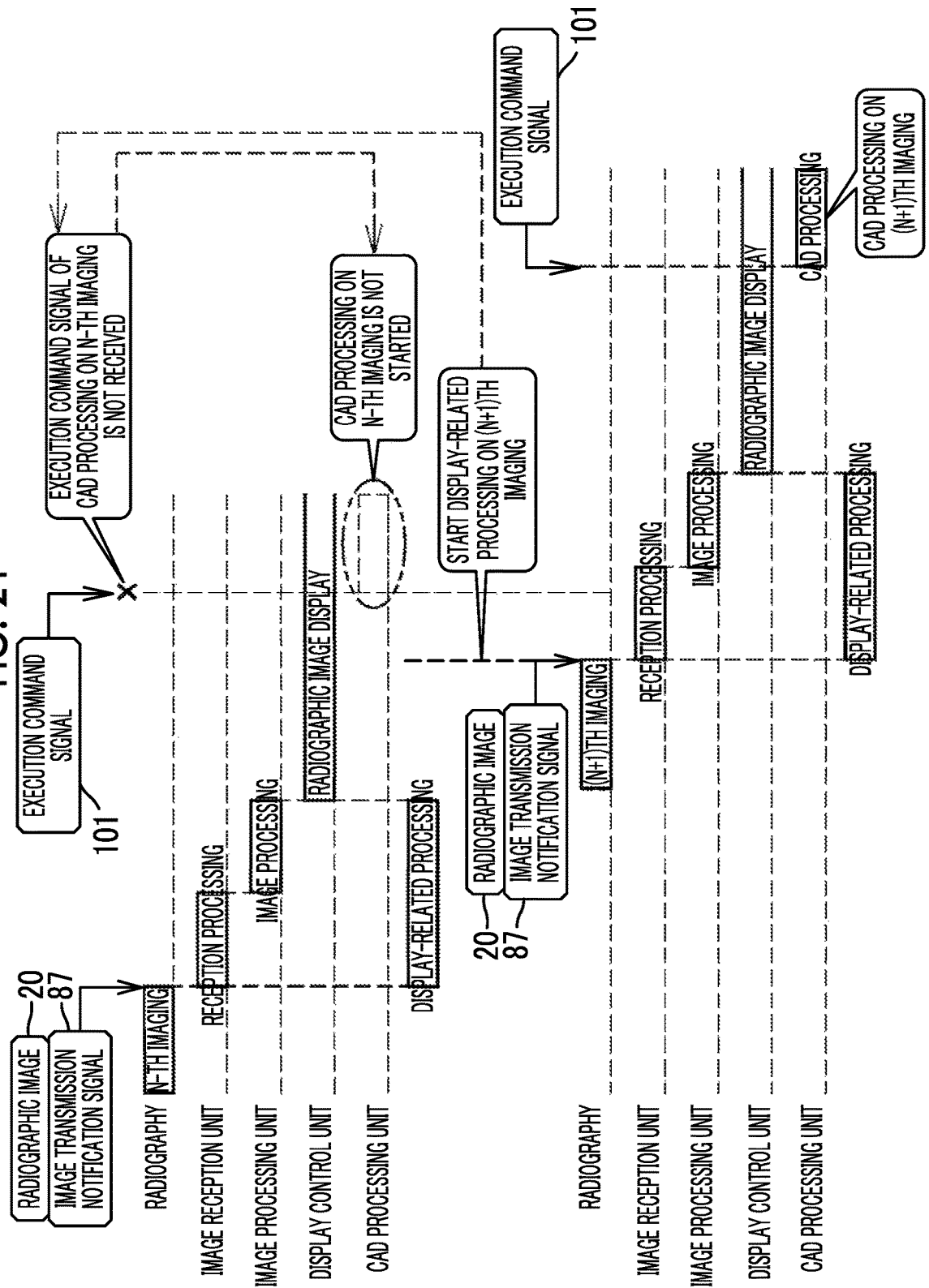
FIG. 21 is a diagram showing a case where, before the CAD processing on the N-th imaging is executed in response to the execution instruction signal, the (N+1)th imaging is performed, and display-related processing on the (N+1)th imaging is started.

In contrast, FIG. 21 shows a case where, before the CAD processing on the N-th imaging is executed in response to the execution instruction signal 101, the (N+1)th imaging is performed, and the display-related processing on the (N+1)th imaging is started. In this case, in a case where the CAD processing on the N-th imaging is started in response to the execution instruction signal 101, since the CAD processing on the N-th imaging competes with the display-related processing on the (N+1)th imaging, the main control unit 71 does not allow the reception unit 65 to receive the execution instruction signal 101 of the CAD processing on the N-th imaging. That is, as in the case of FIG. 10, the main control unit 71 prohibits the execution of the CAD processing while the display-related processing is being executed, as the priority processing.

As a method of not allowing the execution instruction signal 101 of the CAD processing on the N-th imaging to be received, for example, a method in which the CAD processing execution button 100 is brought into non-display or grayed out such that the operator OP cannot select the CAD processing execution button 100 can be employed. Alternatively, a method in which, while the CAD processing execution button 100 is displayed in a selectable form without change, even though the execution instruction signal 101 is received in the reception unit 65, the execution instruction signal 101 is neglected can be employed. In the latter method, in a case where the CAD processing execution button 100 is selected, it is preferable that a message "The execution of the CAD processing is not being received." is pop-up displayed.

After the display-related processing on the (N+1)th imaging is ended, in a case where the execution instruction signal 101 is received in the reception unit 65, the main control unit 71 makes the CAD processing unit 70 execute the CAD processing on the (N+1)th imaging.

Figure 22:
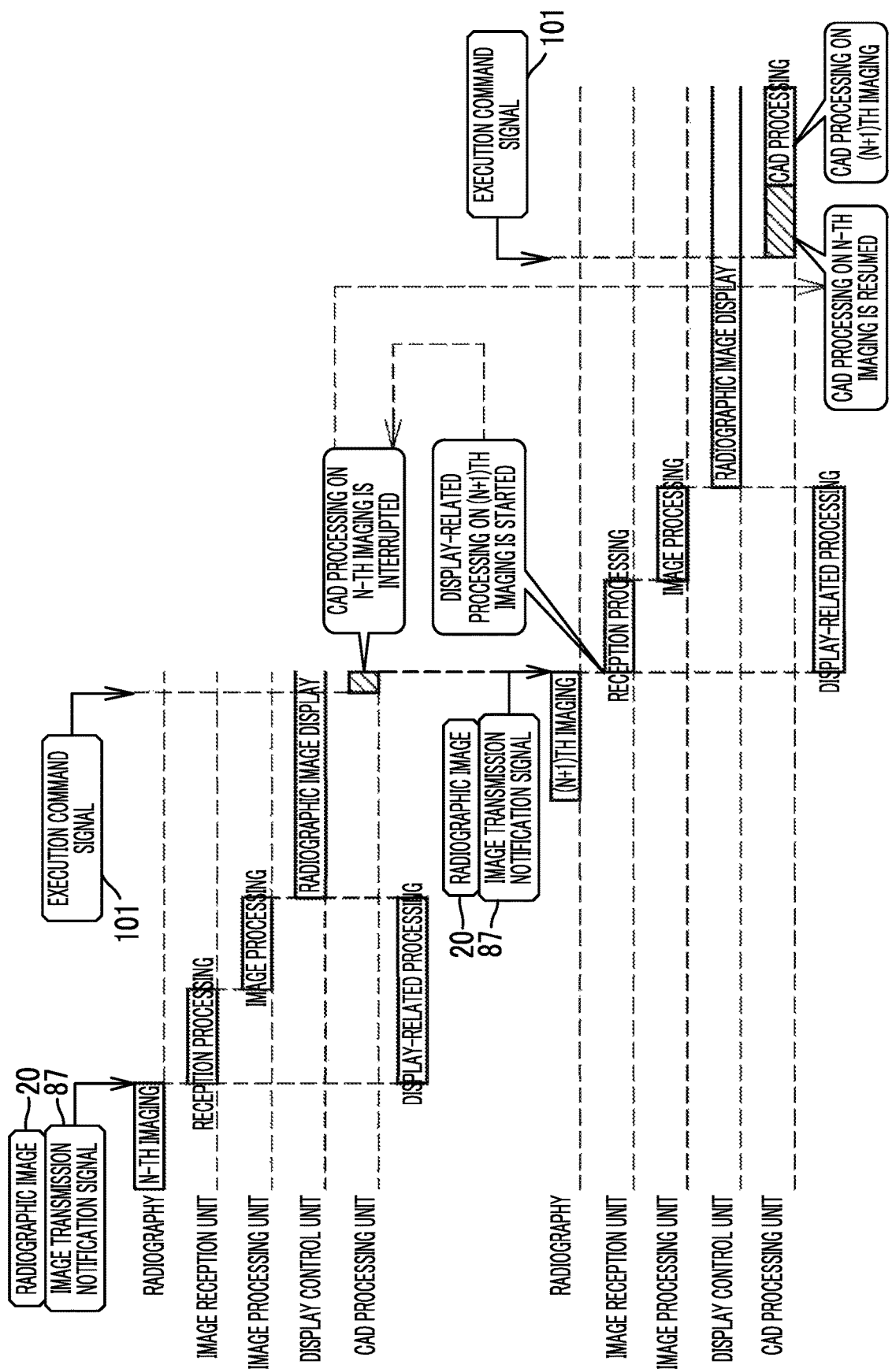
FIG. 22 is a diagram showing a case where, while the CAD processing on the N-th imaging is being executed in response to the execution instruction signal, the (N+1)th imaging is performed, and the display-related processing on the (N+1)th imaging is started.

FIG. 22 shows a case where the (N+1)th imaging is performed while the CAD processing on the N-th imaging is being executed in response to the execution instruction signal 101. In this case, as in the case of FIG. 11, since the CAD processing on the N-th imaging and the display-related processing on the (N+1)th imaging compete with each other, the main control unit 71 interrupts the CAD processing on the N-th imaging and starts the display-related processing on the (N+1)th imaging, as the priority processing.

After the display-related processing on the (N+1)th imaging is ended, in a case where the execution instruction signal 101 is received in the reception unit 65, as in the case of FIG. 11, the main control unit 71 makes the CAD processing unit 70 automatically resume the interrupted CAD processing on N-th imaging. The main control unit 71 subsequently makes the CAD processing unit 70 execute the CAD processing on the (N+1)th imaging after the CAD processing on the N-th imaging is ended.

In this way, in the second embodiment, the execution instruction signal 101 of the CAD processing from the operator OP is received in the reception unit 65 and the CAD processing is executed. For this reason, it is possible to entrust the operator OP with selecting whether or not to execute the CAD processing, and to restrain the CAD processing from being executed on the radiographic image 20 for which the CAD processing is not required, such as the radiographic image 20 obtained by failed imaging. It is possible to reduce a scene where the display-related processing and the CAD processing compete with each other, compared to a case where the CAD processing is automatically executed.

An aspect where the CAD processing automatically starts and an aspect where the CAD processing is executed in a case where there is the execution instruction of the CAD processing from the operator OP may be switched.

Third Embodiment

In the respective embodiments described above, although the interrupted CAD processing is automatically resumed, the technique of the present disclosure is not limited thereto. As in a third embodiment shown in FIGS. 23 to 25, a selection instruction from the operator OP regarding whether or not to resume the interrupted CAD processing may be received.

Figure 23:
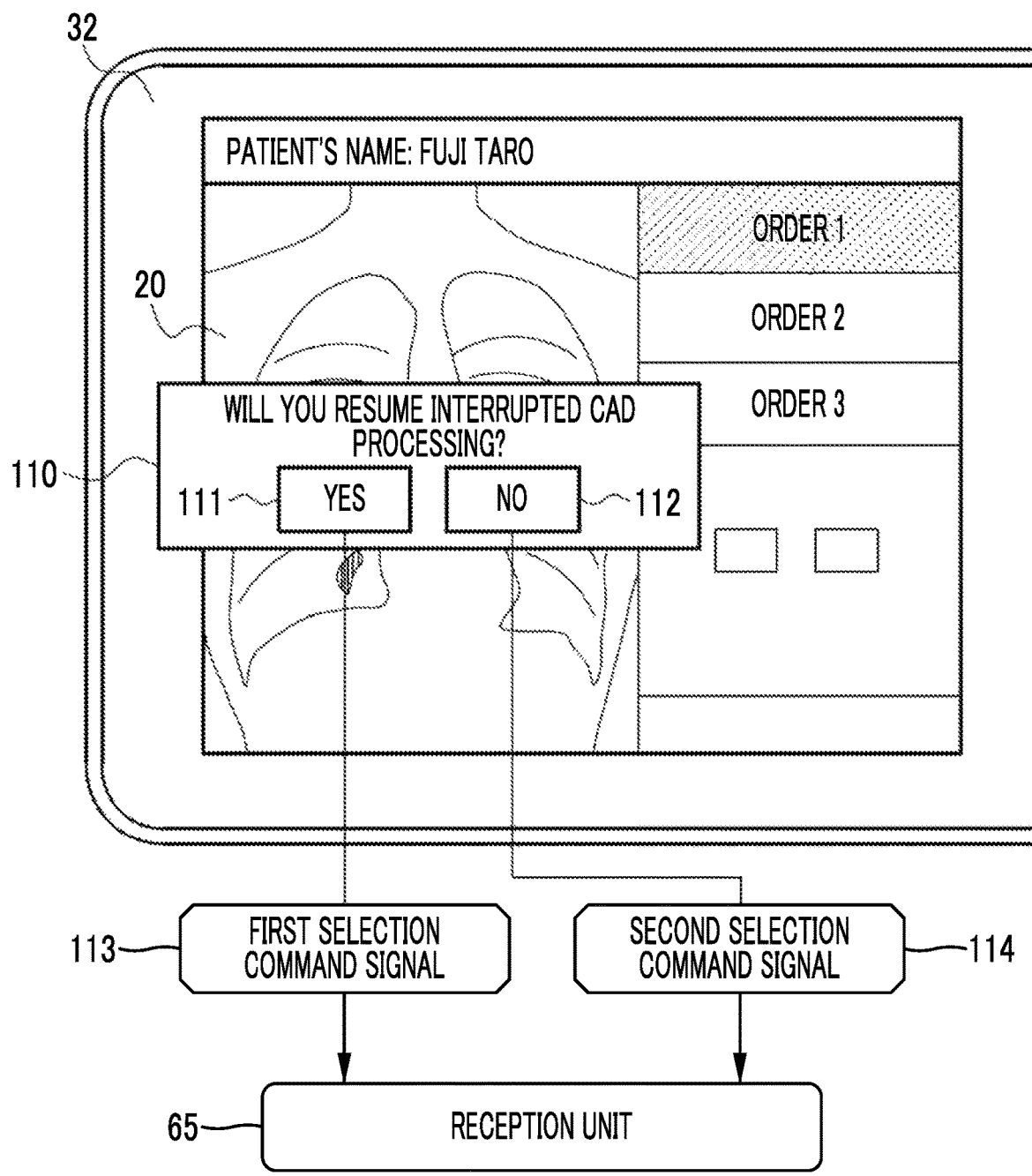
FIG. 23 is a diagram showing a third embodiment in which a selection instruction from an operator regarding whether or not to resume interrupted CAD processing is received.

As shown in FIG. 23, in a case where the CAD processing on the N-th imaging is interrupted, the display control unit 69 displays a dialog box 110 on the display 32 after ending the display-related processing on the (N+1)th imaging. In the dialog box 110, a YES button 111 for inputting a selection instruction to resume the interrupted CAD processing on the N-th imaging and a NO button 112 for inputting a selection instruction not to resume the interrupted CAD processing on the N-th imaging are disposed. The operator OP selects the YES button 111 in a case where the operator OP wants to resume the interrupted CAD processing on the N-th imaging and selects the NO button 112 in a case where the operator OP does not want to resume the interrupted CAD processing on N-th imaging. In a case where the YES button 111 is selected by the operator OP, a first selection instruction signal 113 indicating the selection instruction to resume the interrupted CAD processing on the N-th imaging is output from the display 32 and is received in the reception unit 65. With this, the CAD processing on the N-th imaging is resumed in the CAD processing unit 70. In contrast, in a case where the NO button 112 is selected by the operator OP, a second selection instruction signal 114 indicating the selection instruction not to resume the interrupted CAD processing on the N-th imaging is output from the display 32 and is received in the reception unit 65. In this case, the CAD processing on the N-th imaging is not resumed.

Figure 24:
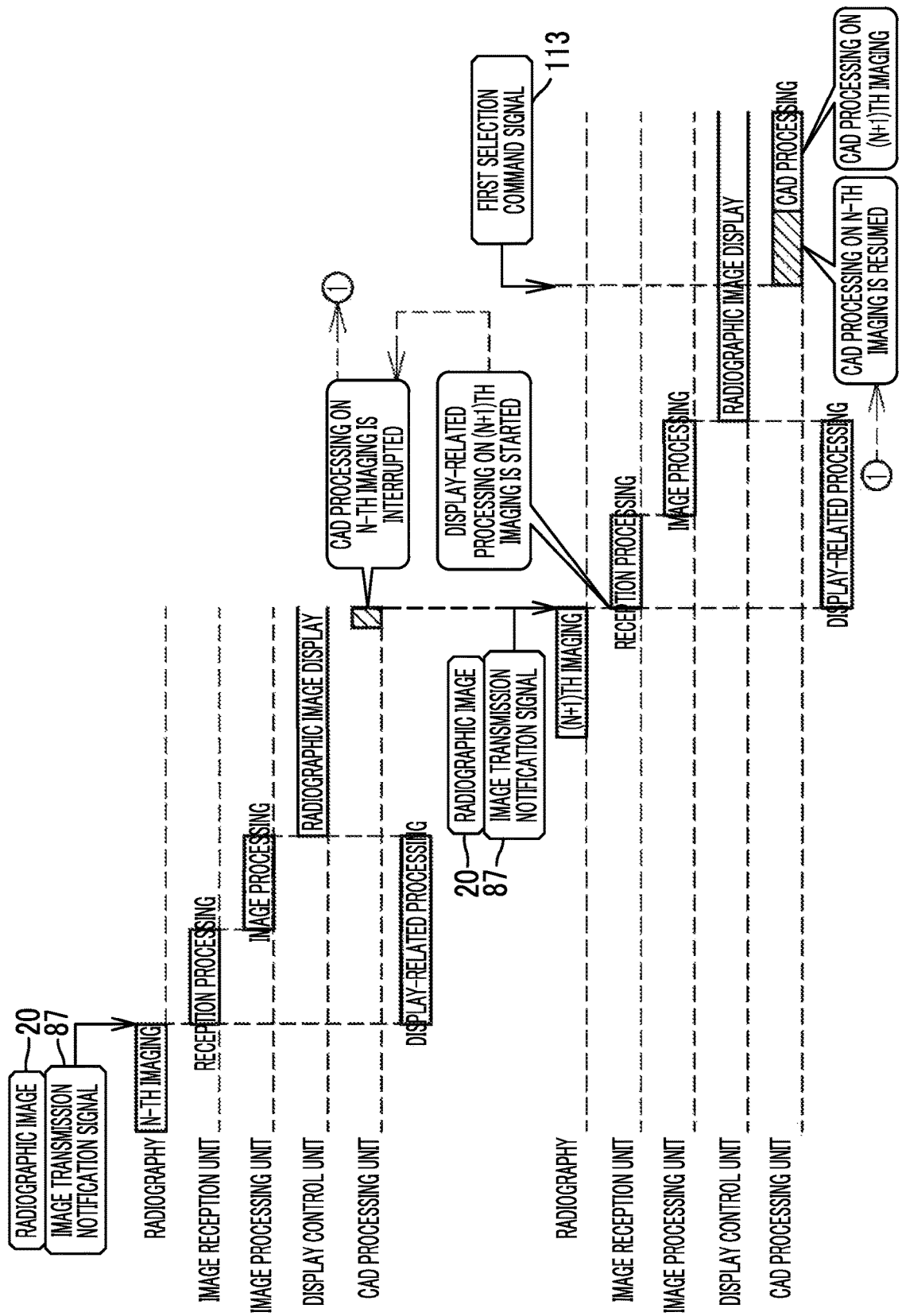
FIG. 24 is a diagram showing a case where, while CAD processing on N-th imaging is being executed, in a case where (N+1)th imaging is performed, an operator issues a selection instruction to resume the interrupted CAD processing.
Figure 25:
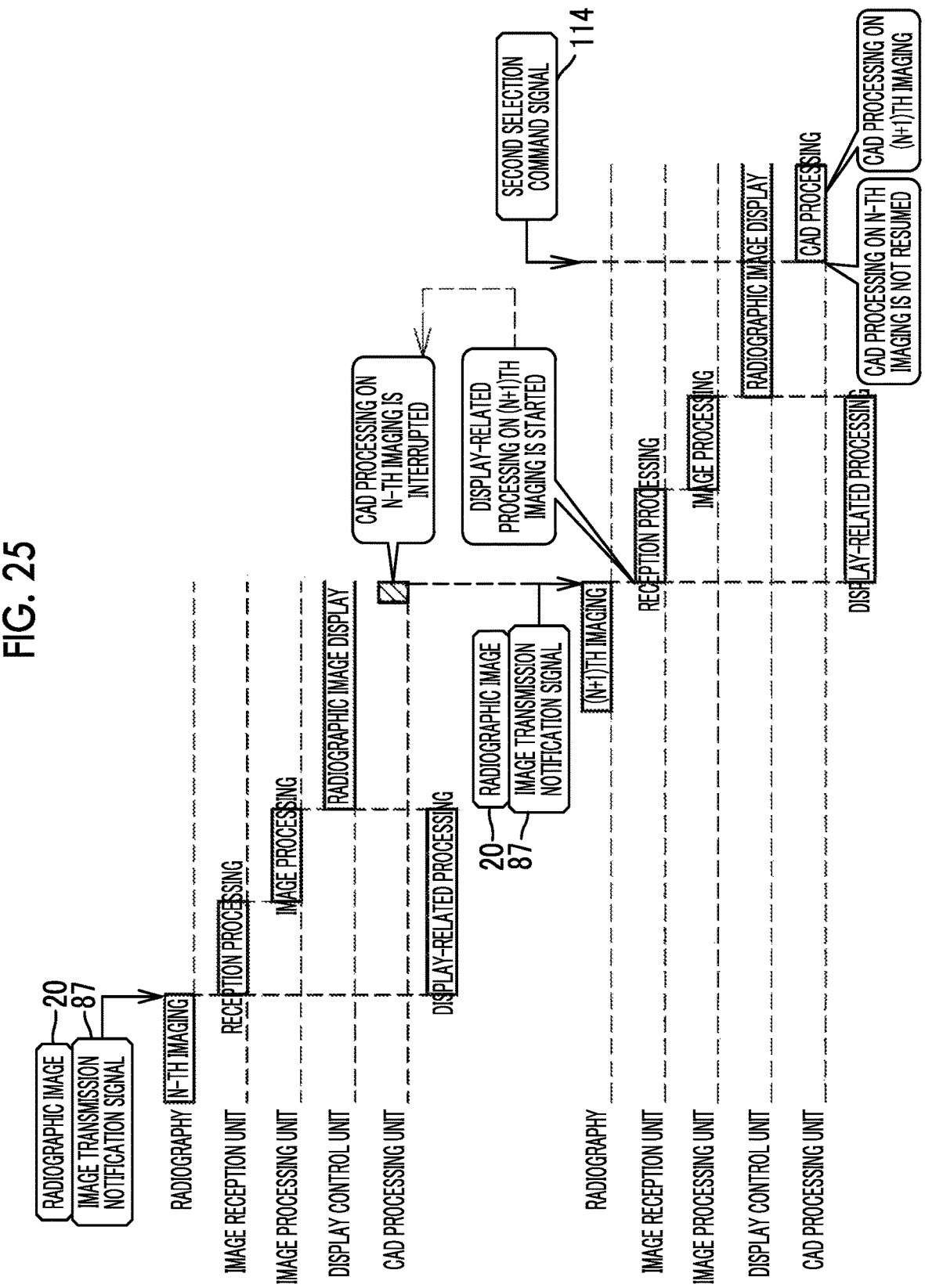
FIG. 25 is a diagram showing a case where, while the CAD processing on the N-th imaging is being executed, in a case where the (N+1)th imaging is performed, the operator issues a selection instruction to not resume the interrupted CAD processing.

Both FIGS. 24 and 25 show a case where the (N+1)th imaging is performed while the CAD processing on the N-th imaging is being executed. In this case, as in the case of FIG. 11, the main control unit 71 interrupts the CAD processing on the N-th imaging and starts the display-related processing on the (N+1)th imaging, as the priority processing.

FIG. 24 shows a case where, after the display-related processing on the (N+1)th imaging is ended, the YES button 111 of the dialog box 110 is selected by the operator OP, and the first selection instruction signal 113 is received in the reception unit 65. In this case, the main control unit 71 makes the CAD processing unit 70 resume the interrupted CAD processing on the N-th imaging. The main control unit 71 subsequently makes the CAD processing unit 70 execute the CAD processing on the (N+1)th imaging after the CAD processing on the N-th imaging is ended.

In contrast, FIG. 25 shows a case where, after the display-related processing on the (N+1)th imaging is ended, the NO button 112 of the dialog box 110 is selected by the operator OP, and the second selection instruction signal 114 is received in the reception unit 65. In this case, the main control unit 71 does not make the CAD processing unit 70 resume the interrupted CAD processing on the N-th imaging and makes the CAD processing unit 70 execute the CAD processing on the (N+1)th imaging.

In this way, in the third embodiment, after the display-related processing on the (N+1)th imaging ends, the selection instruction from the operator OP regarding whether or not to resume the interrupted CAD processing on the N-th imaging is received in the reception unit 65. Then, in a case where the first selection instruction signal 113 indicating the selection instruction to resume the interrupted CAD processing on the N-th imaging is received, the CAD processing unit 70 resumes the interrupted CAD processing on the N-th imaging. In contrast, in a case where the second selection instruction signal 114 indicating the selection instruction not to resume the interrupted CAD processing on the N-th imaging is received, the CAD processing unit 70 does not resume the interrupted CAD processing on the N-th imaging. For this reason, as in the second embodiment described above, it is possible to entrust the operator OP with selecting whether or not to resume the interrupted CAD processing, and to restrain the CAD processing from being resumed on the radiographic image 20 for which the CAD processing is not required, such as the radiographic image 20 obtained by failed imaging. It is possible to reduce a scene where the display-related processing and the CAD processing compete with each other, compared to a case where the CAD processing is automatically resumed.

An aspect where the interrupted CAD processing is automatically resumed and an aspect where the selection instruction from the operator OP regarding whether or not to resume the interrupted CAD processing is received may be switched.

In the example of FIG. 10 showing a case where, in a period from when the display-related processing on the N-th imaging is ended to when the CAD processing on the N-th imaging is started, the (N+1)th imaging is performed, the display-related processing on the (N+1)th imaging is started, and the start of the CAD processing on N-th imaging is postponed, a selection instruction from the operator OP regarding whether or not to make the CAD processing unit 70 execute the CAD processing on the N-th imaging of which the start is postponed may be received.

Fourth Embodiment

In a fourth embodiment shown in FIGS. 26 to 30, whether or not to resume the interrupted CAD processing on N-th imaging is decided depending on whether or not the (N+1)th imaging is reimaging of the N-th imaging.

Figure 26:
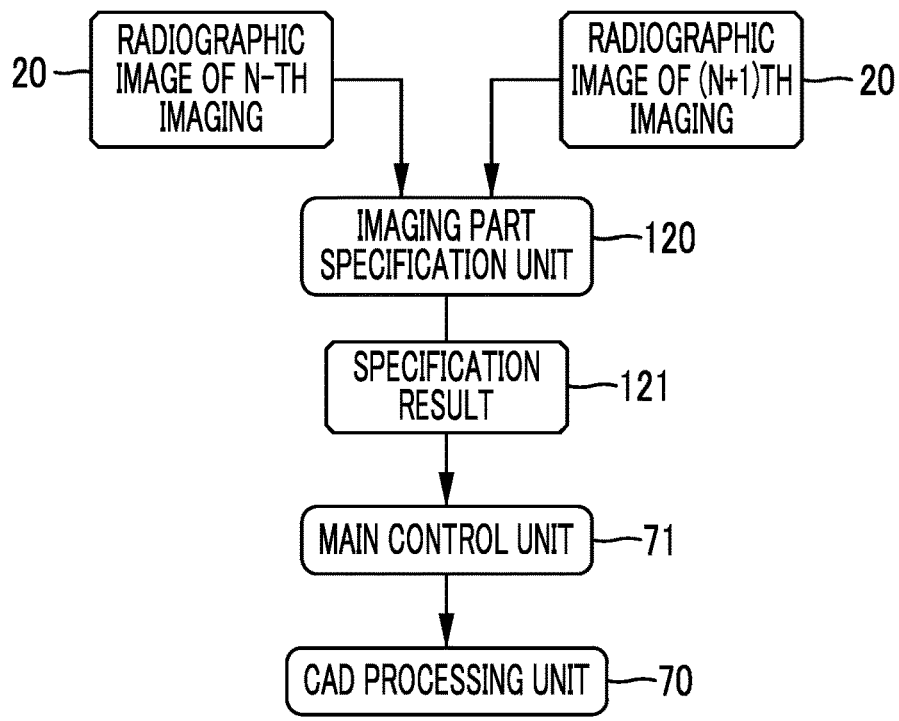
FIG. 26 is a block diagram showing functions of a CPU of a fourth embodiment.

In FIG. 26, a CPU 53 of a console 55 of the fourth embodiment functions as an imaging part specification unit 120, in addition to the respective units 65 to 71 (in FIG. 26, only the CAD processing unit 70 and the main control unit 71 are shown) shown in the first embodiment described above. The imaging part specification unit 120 specifics an imaging part of the N-th imaging from an image of the subject H reflected in the radiographic image 20 on the N-th imaging using a known image recognition technique. Similarly, the imaging part specification unit 120 specifies an imaging part of the (N+1)th imaging from an image of the subject H reflected in the radiographic image 20 on the (N+1)th imaging using a known image recognition technique. The imaging part specification unit 120 outputs a specification result 121 of the imaging part to the main control unit 71. The main control unit 71 controls the operation of the CAD processing unit 70 based on the specification result 121.

Figure 27:
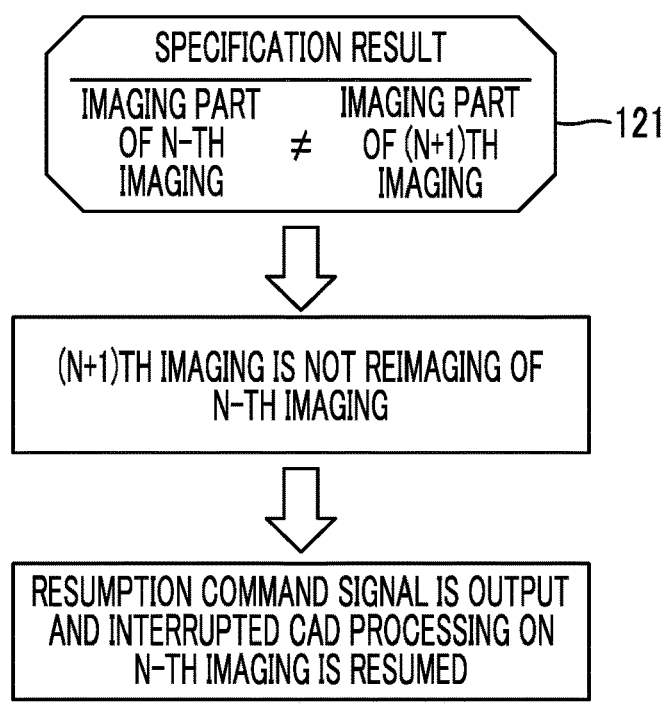
FIG. 27 is a diagram showing a case where a specification result of an imaging part has the content that an imaging part of N-th imaging and an imaging part of (N+1)th imaging are not the same.

FIG. 27 shows a case where the specification result 121 has the content that the imaging part of the N-th imaging and the imaging part of the (N+1)th imaging are not the same. In this case, the main control unit 71 determines that the (N+1)th imaging is not reimaging of the N-th imaging and outputs a resumption instruction signal 122 (see FIG. 29) for making the CAD processing unit 70 resume the interrupted CAD processing on the N-th imaging to the CAD processing unit 70. The CAD processing unit 70 receives the resumption instruction signal 122 and resumes the interrupted CAD processing on the N-th imaging.

Figure 28:
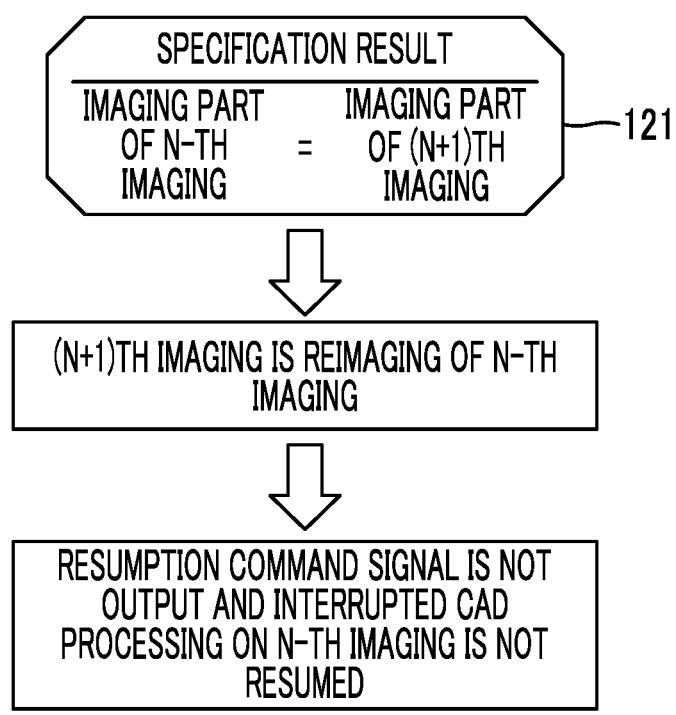
FIG. 28 is a diagram showing a case where the specification result of the imaging part has the content that the imaging part of the N-th imaging and the imaging part of the (N+1)th imaging are the same.

In contrast, FIG. 28 shows a case where the specification result 121 has the content that the imaging part of the N-th imaging and the imaging part of the (N+1)th imaging are the same. In this case, the main control unit 71 determines that the (N+1)th imaging is reimaging of the N-th imaging and does not output the resumption instruction signal 122 to the CAD processing unit 70. Since the resumption instruction signal 122 is not input, the CAD processing unit 70 does not resume the interrupted CAD processing on the N-th imaging.

Figure 29:
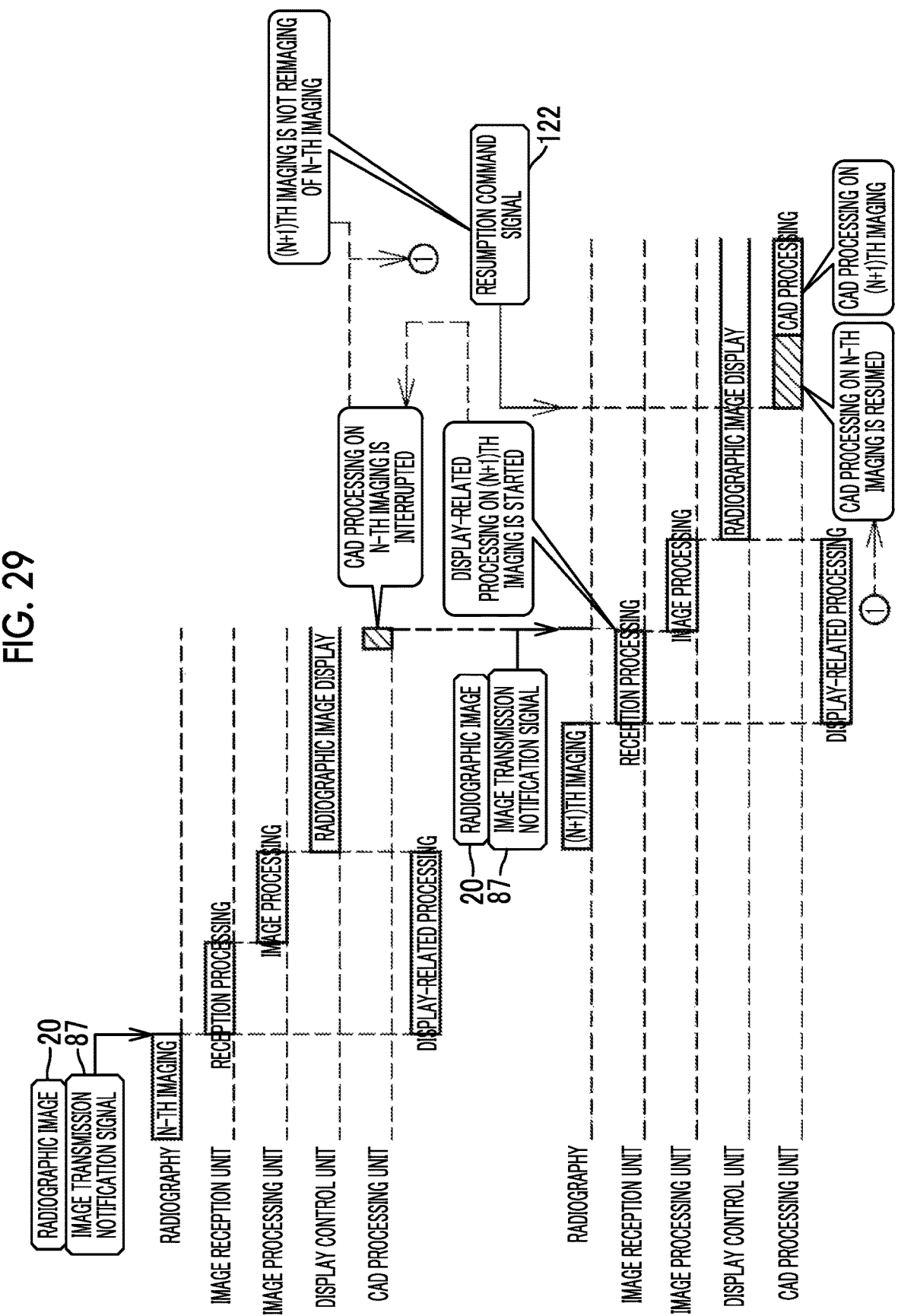
FIG. 29 is a diagram showing a case where, while CAD processing on N-th imaging is being executed, in a case where (N+1)th imaging is performed, a specification result of an imaging part has the content that an imaging part of the N-th imaging and an imaging part of the (N+1)th imaging are not the same.
Figure 30:
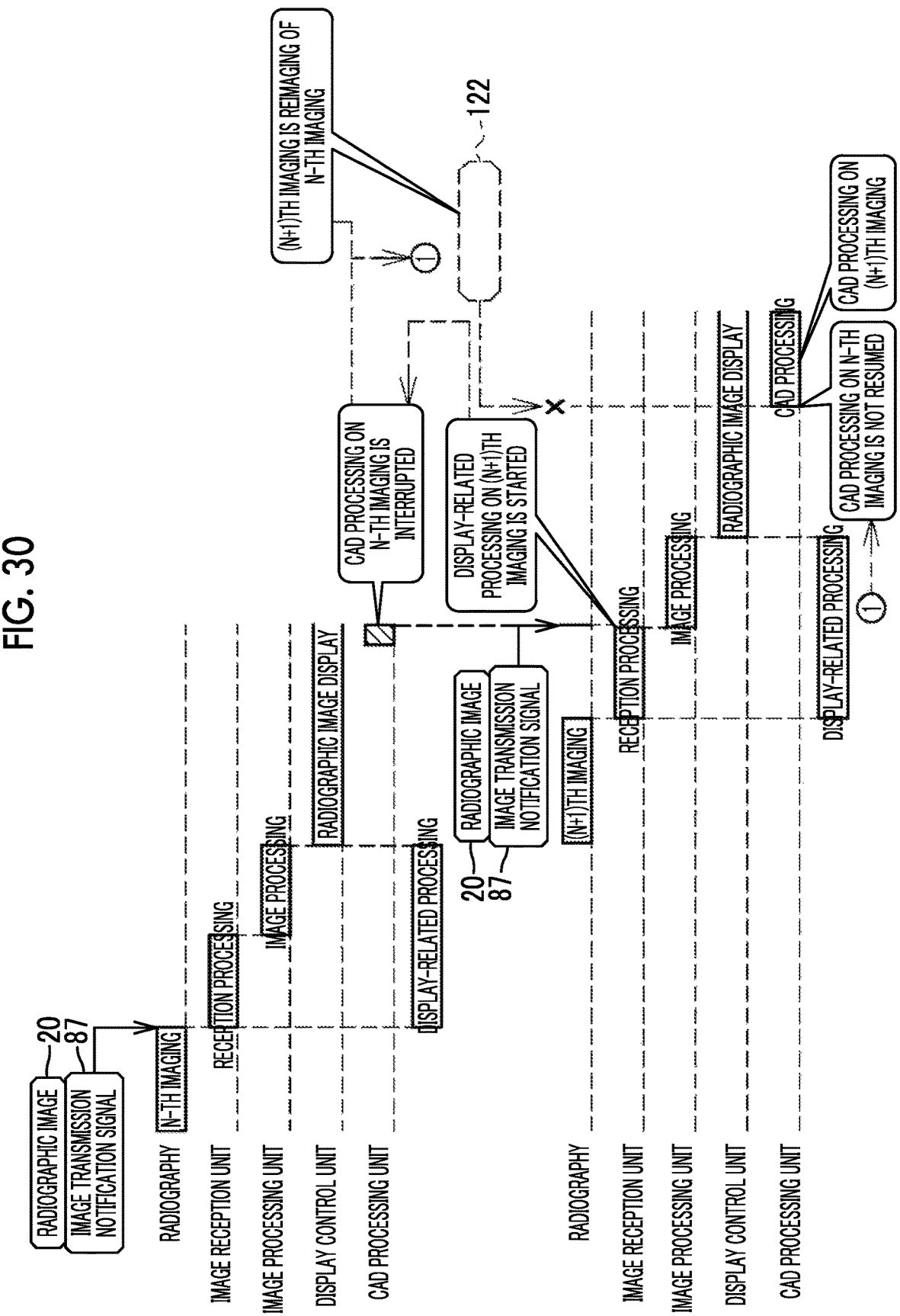
FIG. 30 is a diagram showing a case where, while the CAD processing on the N-th imaging is being executed, in a case where the (N+1)th imaging is performed, the specification result of the imaging part has the content that the imaging part of the N-th imaging and the imaging part of the (N+1)th imaging are the same.

Both FIGS. 29 and 30 show a case where the (N+1)th imaging is performed while the CAD processing on the N-th imaging is being executed. In this case, as in the case of FIG. 11, the main control unit 71 interrupts the CAD processing on the N-th imaging and starts the display-related processing on the (N+1)th imaging, as the priority processing.

FIG. 29 shows a case where the specification result 121 of the imaging part specification unit 120 has the content shown in FIG. 27 that the imaging part of the N-th imaging and the imaging part of the (N+1)th imaging are not the same. In this case, the main control unit 71 outputs the resumption instruction signal 122 to the CAD processing unit 70 after the display-related processing on the (N+1)th imaging is ended. With this, the main control unit 71 makes the CAD processing unit 70 resume the interrupted CAD processing on the N-th imaging. The main control unit 71 subsequently makes the CAD processing unit 70 execute the CAD processing on the (N+1)th imaging after the CAD processing on the N-th imaging is ended.

In contrast, FIG. 30 shows a case where the specification result 121 of the imaging part specification unit 120 has the content shown in FIG. 28 that the imaging part of the N-th imaging and the imaging part of the (N+1)th imaging are the same. In this case, the main control unit 71 does not output the resumption instruction signal 122 to the CAD processing unit 70 after the display-related processing on the (N+1)th imaging is ended. With this, the main control unit 71 does not make the CAD processing unit 70 resume the interrupted CAD processing on the N-th imaging and makes the CAD processing unit 70 execute the CAD processing on the (N+1)th imaging.

In this way, in the fourth embodiment, the CAD processing unit 70 resumes the interrupted CAD processing on the N-th imaging in a case where the (N+1)th imaging is not reimaging of the N-th imaging and does not resume the interrupted CAD processing on the N-th imaging in a case where the (N+1)th imaging is reimaging of the N-th imaging. A case where the (N+1)th imaging is reimaging of the N-th imaging means that imaging of the N-th imaging fails. For this reason, it is possible to restrain the CAD processing from being resumed on the radiographic image 20 obtained by failed imaging for which the CAD processing is not required. In the third embodiment described above, although the operator OP needs to select the NO button 112 in a case where the operator OP does not want to resume the interrupted CAD processing, in the fourth embodiment, such an operation is not required. For this reason, not so much time and effort is not required for the operator OP.

In the fourth embodiment, in a case where the imaging part is not the same as in the N-th imaging, the CAD processing unit 70 determines that the (N+1)th imaging is not reimaging of the N-th imaging and resumes the interrupted CAD processing on the N-th imaging, and in a case where the imaging part is the same as in the N-th imaging, the CAD processing unit 70 determines that the (N+1)th imaging is reimaging of the N-th imaging and does not resume the interrupted CAD processing on the N-th imaging. For this reason, it is possible to accurately and easily determine whether or not the (N+1)th imaging is reimaging of the N-th imaging.

Determination regarding whether or not the (N+1)th imaging is reimaging of the N-th imaging may be performed depending on whether or not the subject H is the same as in the N-th imaging, in addition to the imaging part. Specifically, in a case where at least one of the imaging part or the subject H is not the same, determination is made that the (N+1)th imaging is not reimaging of the N-th imaging, and the interrupted CAD processing on the N-th imaging is resumed. In contrast, in a case where both the imaging part and the subject H are the same, determination is made that the (N+1)th imaging is reimaging of the N-th imaging, and the interrupted CAD processing on the N-th imaging is not resumed.

Fifth Embodiment

In the respective embodiments described above, although, in a case where the (N+1)th imaging is performed while the CAD processing on N-th imaging is being executed, as the priority processing, the CAD processing on N-th imaging is interrupted and the display-related processing on the (N+1)th imaging is started, the technique of the present disclosure is not limited thereto. As in a fifth embodiment shown in FIGS. 31 and 32, as the priority processing, the CAD processing on the N-th imaging is not interrupted, a part of resources allocated to the CAD processing on the N-th imaging may be allocated to the display-related processing on the (N+1)th imaging, and the number of resources allocated to the display-related processing on the (N+1)th imaging may be set greater than in the CAD processing on the N-th imaging.

Figure 31:
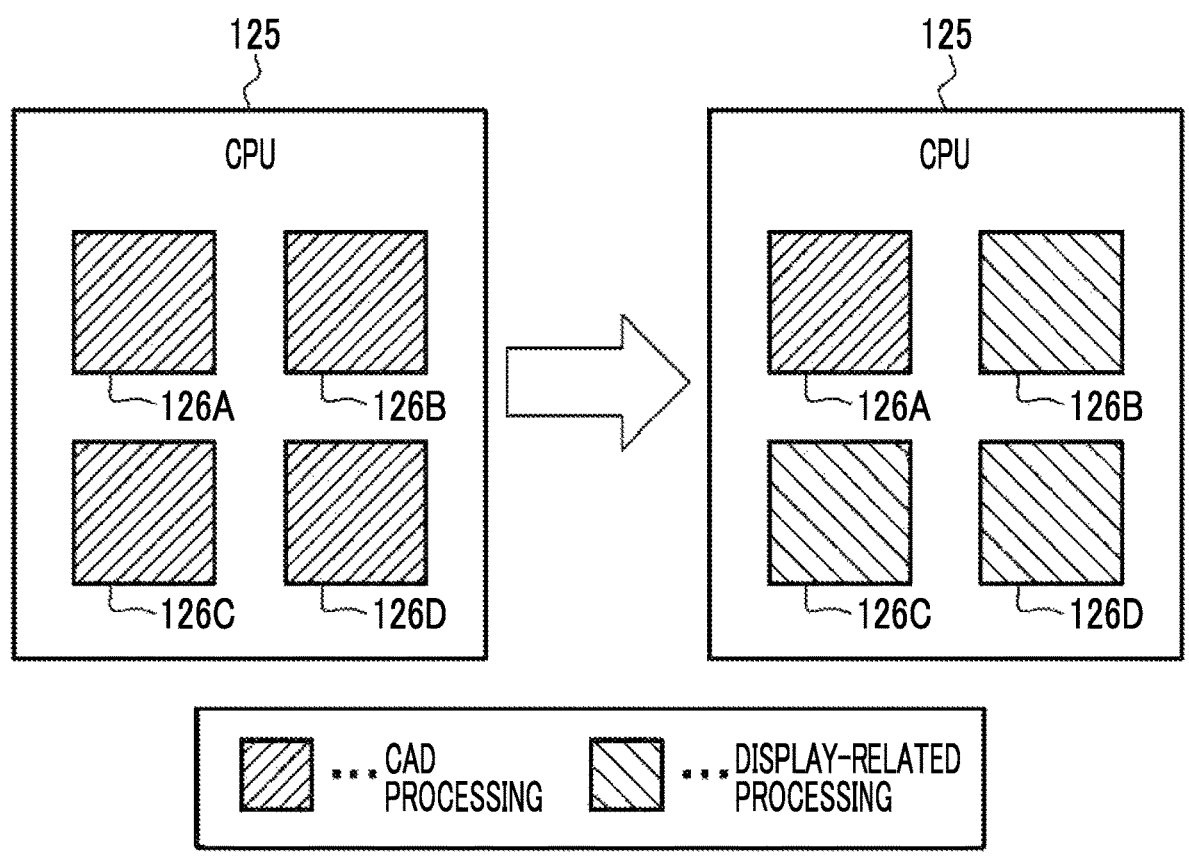
FIG. 31 is a diagram showing an aspect where a function of a display-related processing unit is allocated to three cores of four cores allocated to CAD processing on N-th imaging.

A CPU 125 of a console shown in FIG. 31 has four cores 126A, 126B, 126C, and 126D. Each of the cores 126A to 126D has one thread (not shown). That is, the CPU 125 is a multi-core single-thread CPU. The cores 126A to 126D are an example of "resources" according to the technique of the present disclosure.

In a case of executing the CAD processing on the N-th imaging, as shown on a left side of an arrow, the main control unit 71 allocates the function of the CAD processing unit 70 to all of the four cores 126A to 126D. In contrast, in a case where the (N+1)th imaging is performed while the CAD processing on the N-th imaging is being executed, as shown on a right side of the arrow, the main control unit 71 allocates the function of the display-related processing unit 68 to three cores 126B to 126D among the four cores 126A to 126D allocated to the CAD processing on the N-th imaging to execute the display-related processing on the (N+1)th imaging. The function of the CAD processing unit 70 is continuously allocated to the core 126A to execute the CAD processing on the N-th imaging.

Figure 32:
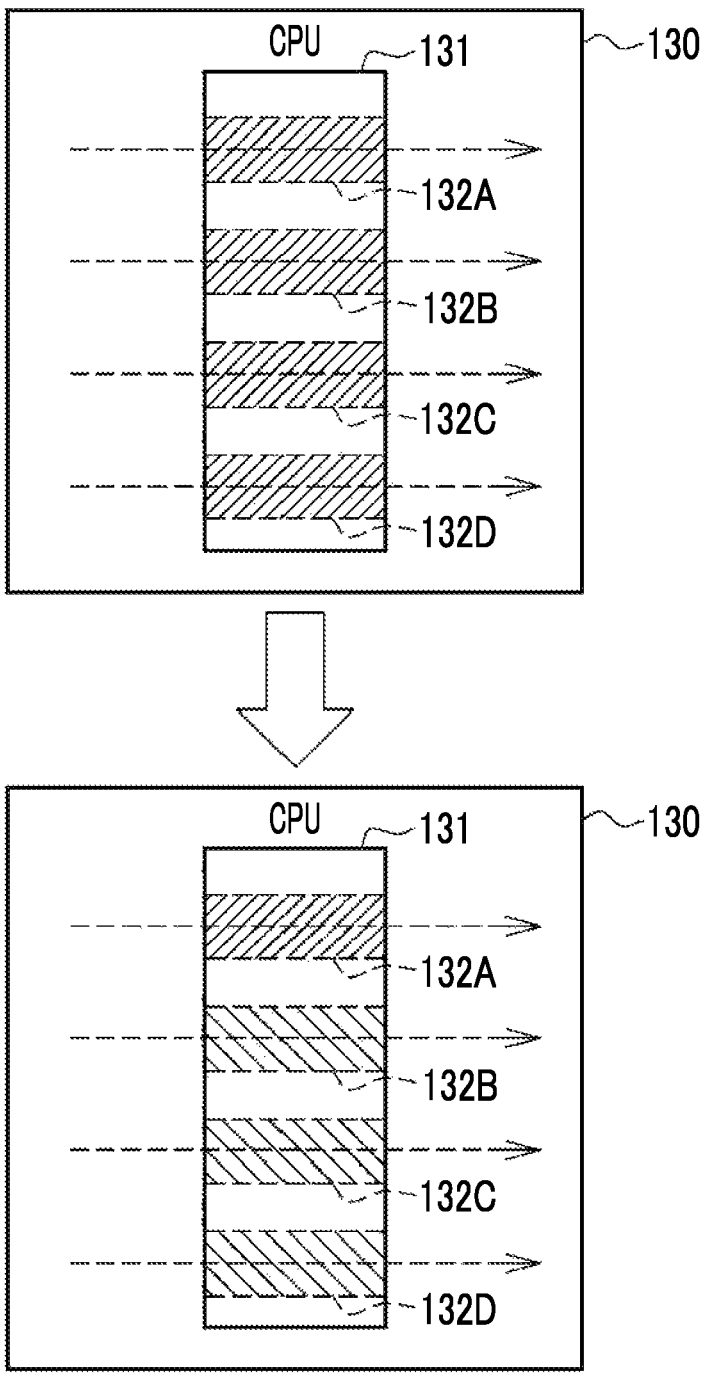
FIG. 32 is a diagram showing an aspect where the function of the display-related processing unit is allocated to three threads of four threads allocated to the CAD processing on the N-th imaging.

A CPU 130 of a console shown in FIG. 32 has one core 131. The core 131 has four threads 132A, 132B, 132C, and 132D. That is, the CPU 130 is a single-core multi-thread CPU. The threads 132A to 132D are an example of "resources" according to the technique of the present disclosure.

In a case of executing the CAD processing on the N-th imaging, as shown on an upside of the arrow, the main control unit 71 allocates the function of the CAD processing unit 70 to all of the four threads 132A to 132D. In contrast, in a case where the (N+1)th imaging is performed while the CAD processing on the N-th imaging is being executed, as shown on a downside of the arrow, the main control unit 71 allocates the function of the display-related processing unit 68 to three threads 132B to 132D among the four threads 132A to 132D allocated to the CAD processing on N-th imaging to execute the display-related processing on the (N+1)th imaging. The function of the CAD processing unit 70 is continuously allocated to the thread 132A to execute the CAD processing on the N-th imaging.

In this way, in the fifth embodiment, the main control unit 71 allocates a part of resources allocated to the CAD processing on the N-th imaging to the display-related processing on the (N+1)th imaging and sets the number of resources allocated to the display-related processing on the (N+1)th imaging greater than in the CAD processing on N-th imaging, as the priority processing. For this reason, it is possible to continuously execute the CAD processing while reducing a concern that the display-related processing is delayed due to the CAD processing.

Although FIG. 31 illustrates the multi-core single-thread CPU 125, and FIG. 32 illustrates the single-core multi-thread CPU 130, the technique of the present disclosure is not limited thereto. A multi-core multi-thread CPU that has a plurality of cores, each having a plurality of threads, may be used.

Sixth Embodiment

In the respective embodiments described above, although one CPU has been illustrated as a processor, the technique of the present disclosure is not limited thereto. As in a sixth embodiment shown in FIG. 33, two sub-processors of a first sub-processor that executes the display-related processing and a second sub-processor that executes the CAD processing may be used.

Figure 33:
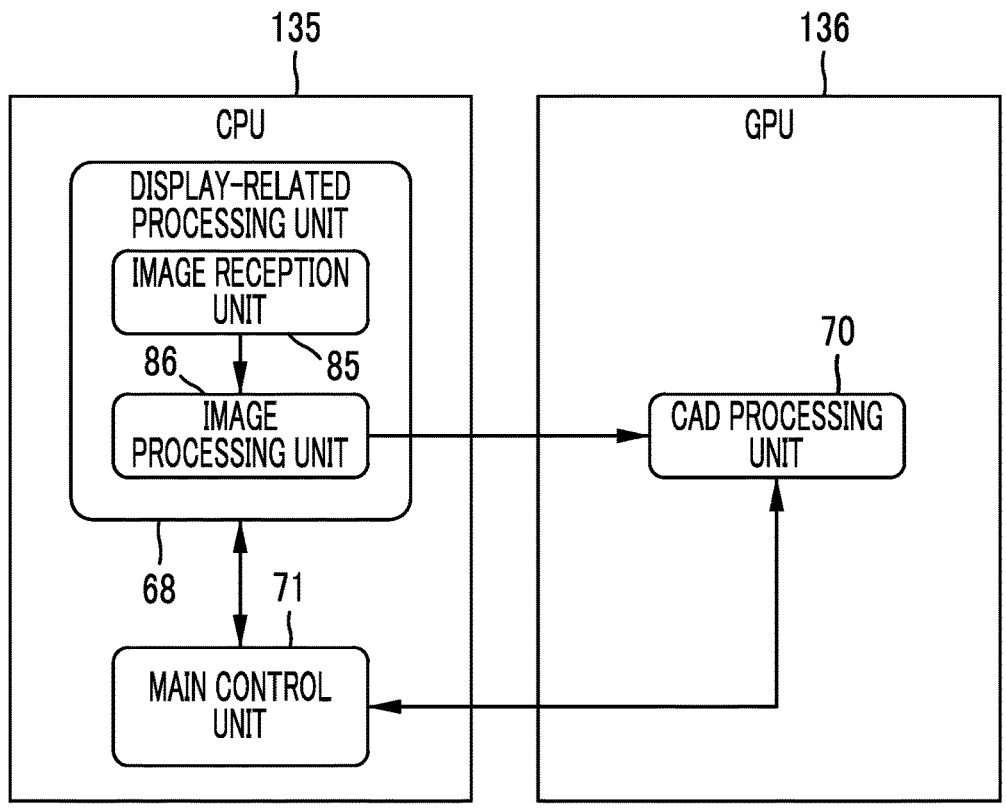
FIG. 33 is a diagram showing a sixth embodiment in which two sub-processors of a first sub-processor that executes display-related processing and a second sub-processor that executes CAD processing are used.

In FIG. 33, a console of the sixth embodiment has a CPU 135 and a graphics processing unit (GPU) 136. The CPU 135 functions as the reception unit 65, the irradiation control unit 66, the cassette control unit 67, the display-related processing unit 68, and the main control unit 71 (in FIG. 33, only the display-related processing unit 68 and the main control unit 71 are shown). The GPU 136 functions as the display control unit 69 and the CAD processing unit 70 (in FIG. 33, only the CAD processing unit 70 is shown). The CPU 135 is an example of a "first sub-processor" according to the technique of the present disclosure. The GPU 136 is an example of a "second sub-processor" according to the technique of the present disclosure.

In this way, in the sixth embodiment, the two-sub-processors of the CPU 135 as a first sub-processor that executes the display-related processing and the GPU 136 as a second sub-processor that executes the CAD processing are provided. For this reason, it is possible to reduce a concern that the display-related processing is delayed due to the CAD processing.

Figure 34:
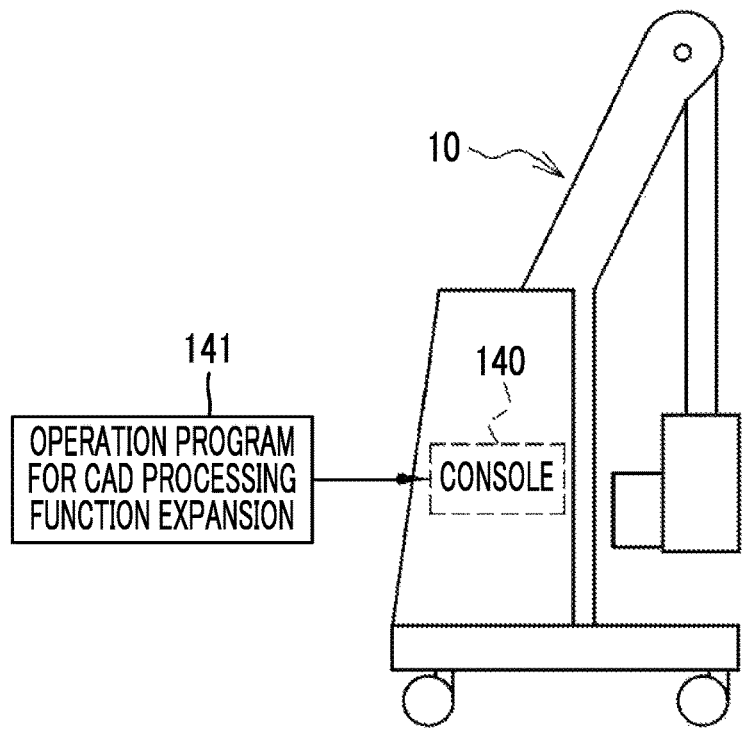
FIG. 34 is a diagram showing an aspect where a function of a CAD processing unit is added to a console incorporated in a mobile radiation generation apparatus through post-mounting.

In the first embodiment described above, although the console 55 that executes the operation program 60 to function as the display-related processing unit 68, the CAD processing unit 70, the main control unit 71, and the like has been illustrated, the technique of the present disclosure is not limited thereto. As shown in FIG. 34, the function of the CAD processing unit 70 may be added through post-mounting by installing an operation program 141 for CAD processing function extension in a console 140 that functions as the display-related processing unit 68, the main control unit 71, and the like, but does not function as the CAD processing unit 70. The operation program 141 for CAD processing function extension is an example of "an operation program for a console for a radiography system" according to the technique of the present disclosure.

Figure 35:
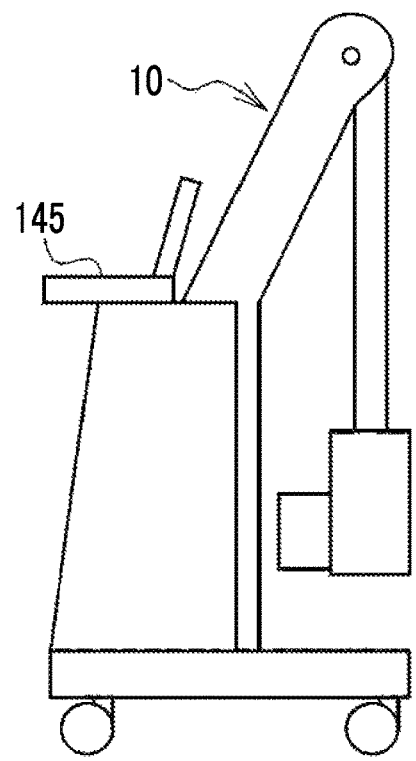
FIG. 35 is a diagram showing an aspect where a notebook type personal computer separated from a mobile radiation generation apparatus is used as a console for a radiography system.

In the first embodiment described above, although the console 55 incorporated in the mobile radiation generation apparatus 10 has been illustrated, the technique of the present disclosure is not limited thereto. For example, as shown in FIG. 35, the operation program 60 may be installed on a notebook type personal computer 145 separated from the mobile radiation generation apparatus 10, and the notebook type personal computer 145 may be used as "a console for a radiography system" according to the technique of the present disclosure. Instead of the notebook type personal computer 145, a tablet terminal may be used as "a console for a radiography system" according to the technique of the present disclosure.

Figure 36:
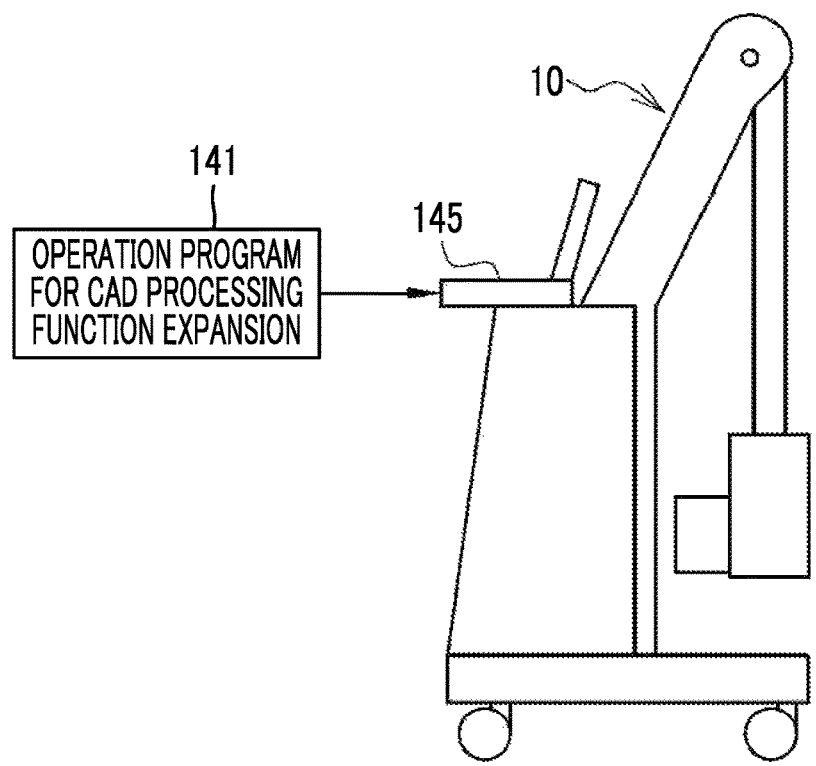
FIG. 36 is a diagram showing an aspect where a function of a CAD processing unit is added to the notebook type personal computer separated from the mobile radiation generation apparatus through post-mounting.

As shown in FIG. 36, even in a case where the notebook type personal computer 145 is used as "a console for a radiography system" according to the technique of the present disclosure, as in the example shown in FIG. 34, the function of the CAD processing unit 70 may be added through post-mounting by installing the operation program 141 for CAD processing function extension.

In a case where the display-related processing and the CAD processing compete with each other, a part of the CAD processing may be entrusted to an external device connected to the console through a network or the like.

In the respective embodiments described above, although the timing at which the image transmission notification signal 87 is received in the image reception unit 85 is defined as the start timing of the display-related processing, the technique of the present disclosure is not limited thereto. A timing at which the operator OP selects the imaging menu 75 on the (N+1)th imaging may be defined as the start timing of the display-related processing. Alternatively, a timing at which the irradiation start instruction signal 78 is received in the reception unit 65 may be defined as the start timing of the display-related processing.

Figure 37:
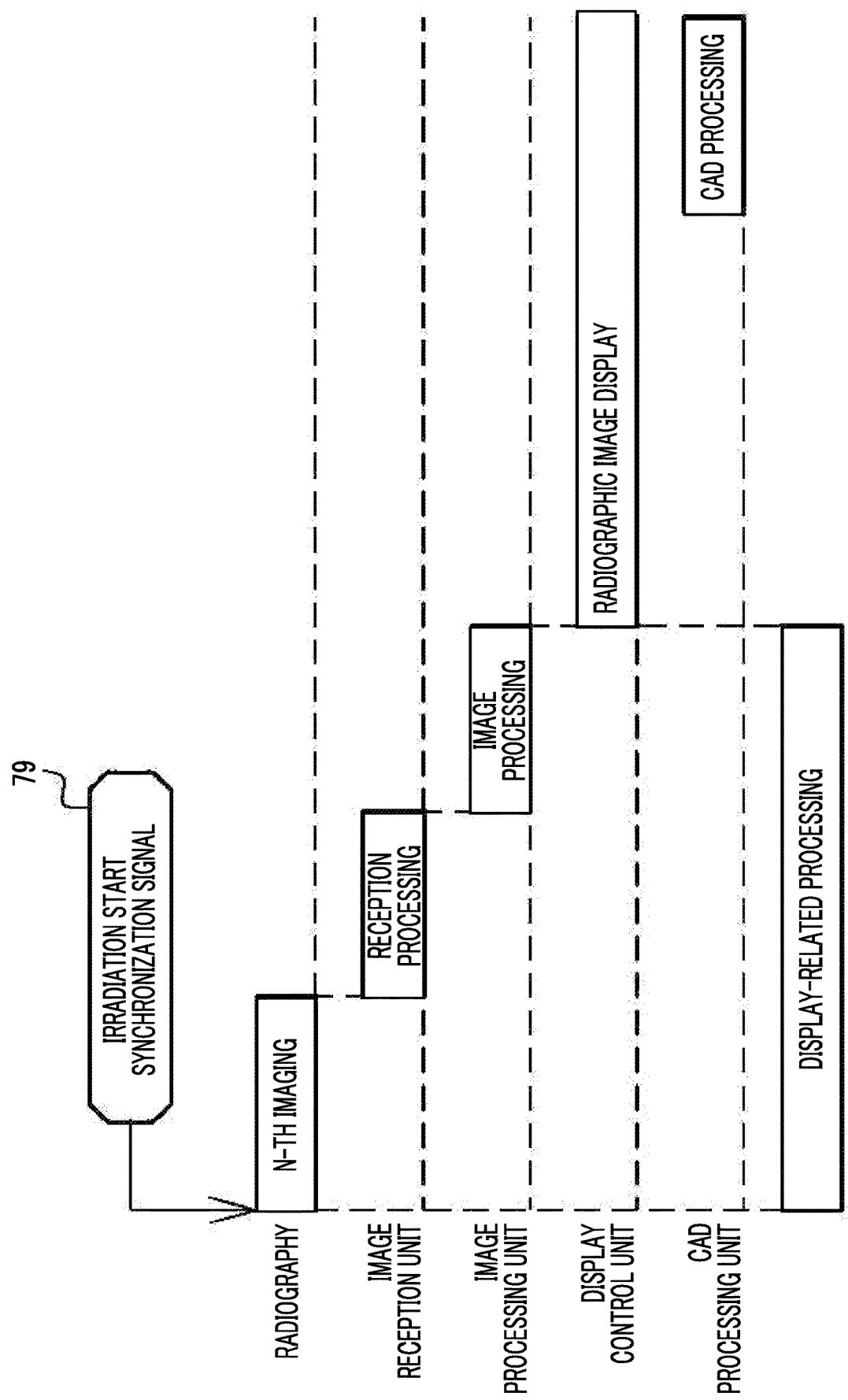
FIG. 37 is a diagram showing an aspect where a timing of transmitting an irradiation start synchronization signal from a cassette control unit to an electronic cassette is set as a start timing of display-related processing.

As shown in FIG. 37, a timing of transmitting the irradiation start synchronization signal 79 from the cassette control unit 67 to the electronic cassette 11 may be defined as the start timing of the display-related processing. In a case where the first embodiment described above is applied to the aspect shown in FIG. 37, a configuration shown in FIGS. 38 to 41 is made. Hereinafter, the contents that have been described in the first embodiment described above will not be repeated.

Figure 38:
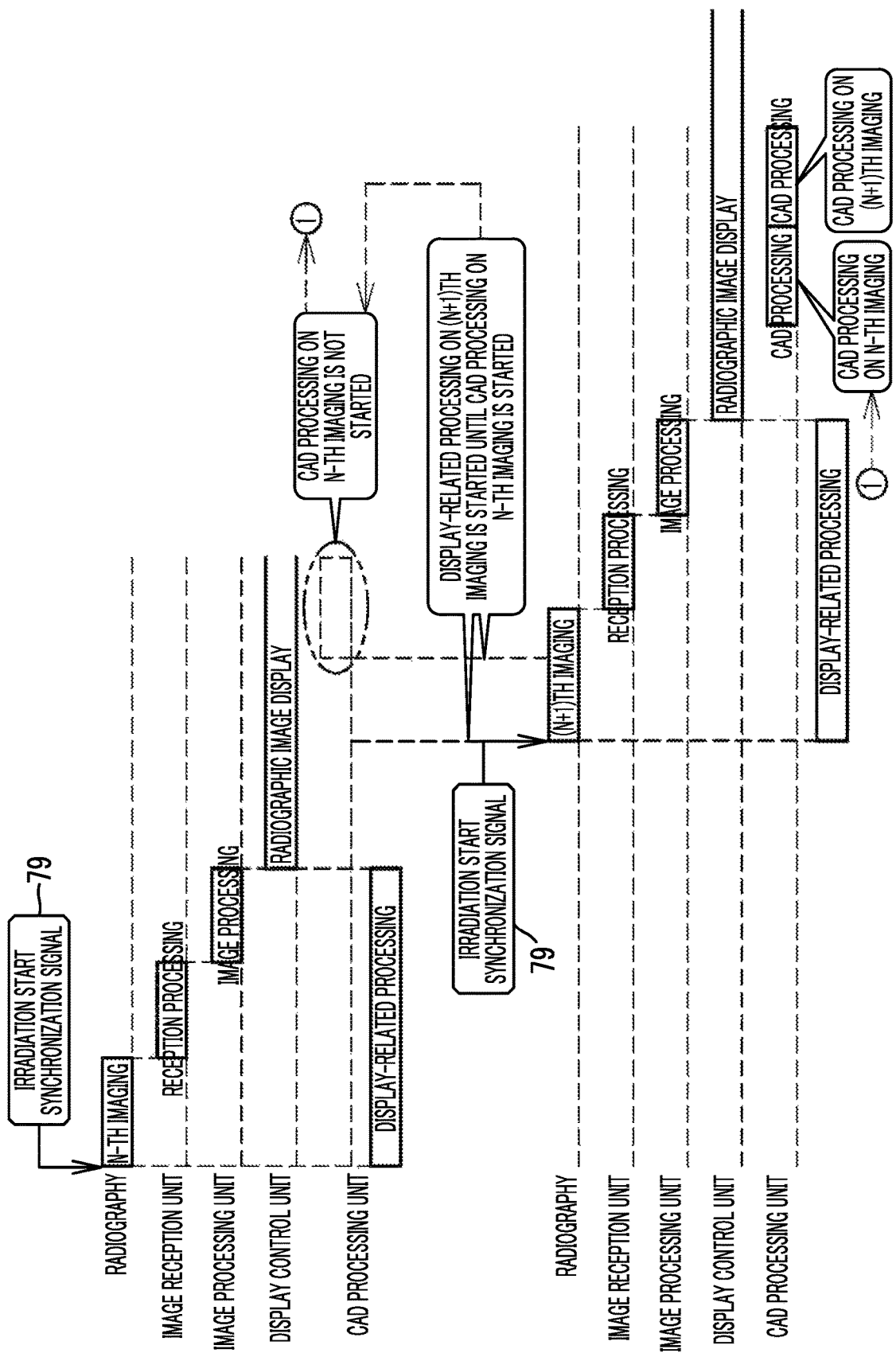
FIG. 38 is a diagram showing a case where, in the aspect shown in FIG. 37, in a period from when display-related processing on N-th imaging is ended to when CAD processing on the N-th imaging is started, (N+1)th imaging is performed, and display-related processing on the (N+1)th imaging is started.

FIG. 38 shows a case where, in a period from when the display-related processing on the N-th imaging is ended to when the CAD processing on the N-th imaging is started, the (N+1)th imaging is performed, the irradiation start synchronization signal 79 is transmitted from the cassette control unit 67 to the electronic cassette 11, and the display-related processing on the (N+1)th imaging is started. In this case, in a case where the CAD processing on the N-th imaging is started without change, since the CAD processing on the N-th imaging competes with the display-related processing on the (N+1)th imaging, the main control unit 71 does not start the CAD processing on the N-th imaging.

Figure 39:
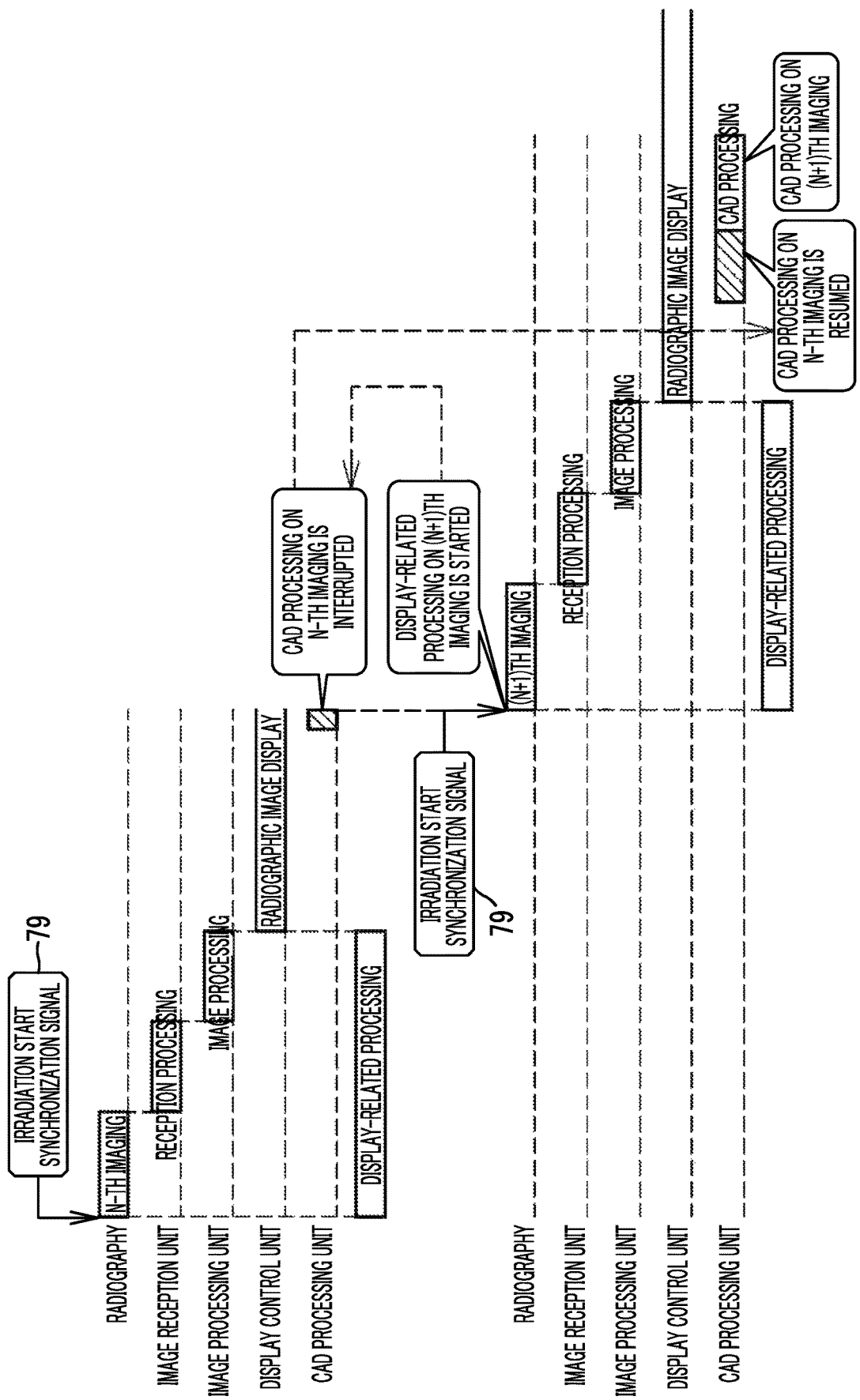
FIG. 39 is a diagram showing a case where, in the aspect shown in FIG. 37, while the CAD processing on the N-th imaging is being executed, the (N+1)th imaging is performed, and the display-related processing on the (N+1)th imaging is started.

FIG. 39 shows a case where, while the CAD processing on the N-th imaging is being executed, the irradiation start synchronization signal 79 is transmitted from the cassette control unit 67 to the electronic cassette 11, and the (N+1)th imaging is performed. In this case, since the CAD processing on the N-th imaging and the display-related processing on the (N+1)th imaging compete with each other, the main control unit 71 interrupts the CAD processing on the N-th imaging and starts the display-related processing on the (N+1)th imaging, as the priority processing.

Figure 40:
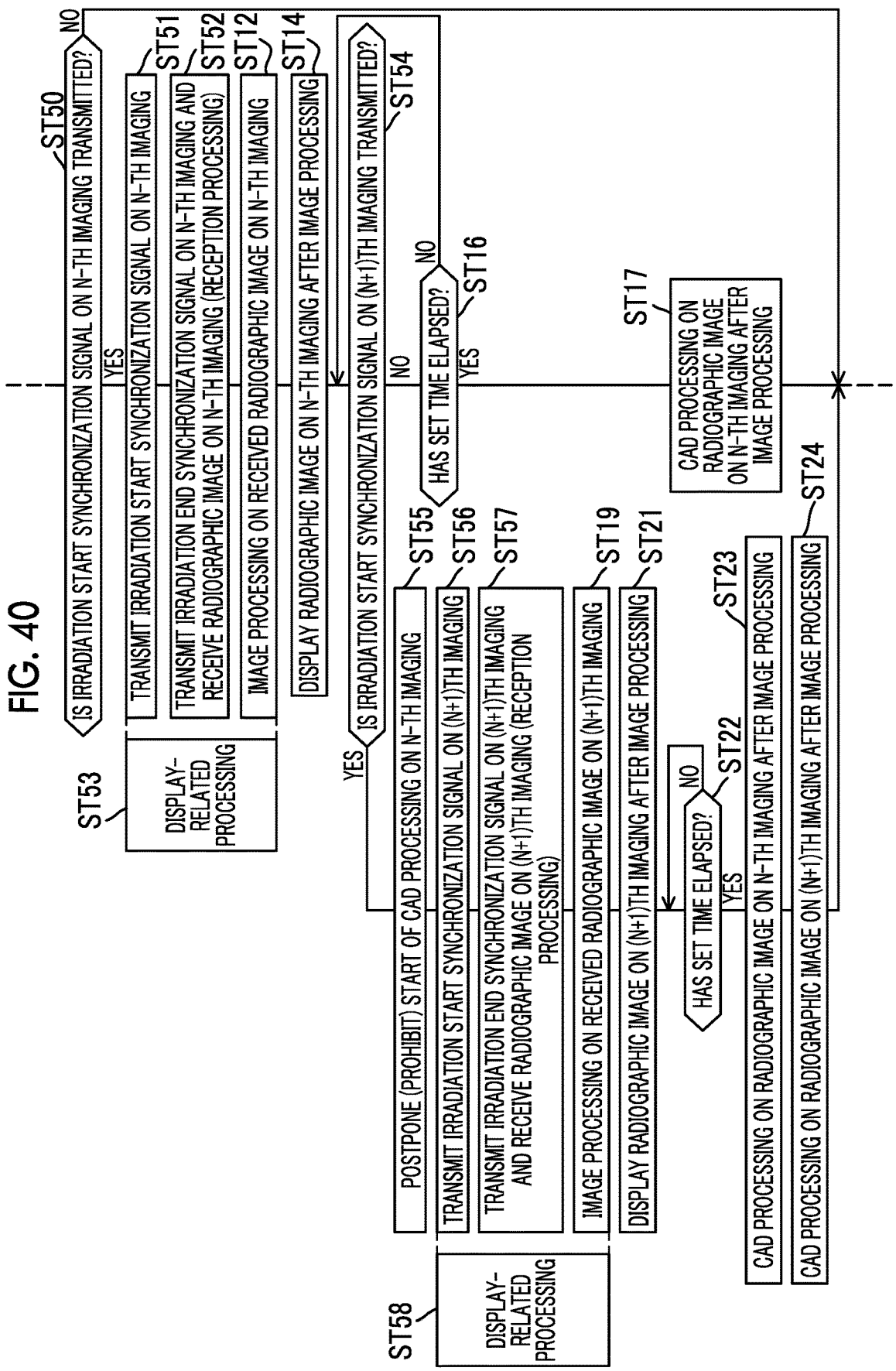
FIG. 40 is a flowchart illustrating the aspect shown in FIG. 38.

FIG. 40 is a flowchart illustrating the aspect shown in FIG. 38. First, in a case where the irradiation start synchronization signal 79 on the N-th imaging is transmitted from the cassette control unit 67 to the electronic cassette 11 (in Step ST50, YES, and Step ST51), when the irradiation time set in the irradiation conditions 76 has elapsed, the irradiation end synchronization signal 80 on the N-th imaging is transmitted from the cassette control unit 67 to the electronic cassette 11. Subsequently, the image transmission notification signal 87 and the radiographic image 20 on the N-th imaging are received in the image reception unit 85 (Step ST52). The radiographic image 20 on the N-th imaging is output from the image reception unit 85 to the image processing unit 86.

In the image processing unit 86, various kinds of image processing are executed on the radiographic image 20 on the N-th imaging (Step ST12). The radiographic image 20 on the N-th imaging after the image processing is output from the image processing unit 86 to the display control unit 69 and the CAD processing unit 70.

As shown in Step ST53, the display-related processing on the N-th imaging is started at a timing at which the irradiation start synchronization signal 79 on the N-th imaging is transmitted from the cassette control unit 67. Then, the display-related processing on the N-th imaging is ended at a timing at which the radiographic image 20 on the N-th imaging after the image processing is output from the image processing unit 86. Step ST53 is an example of a "display-related processing step" according to the technique of the present disclosure.

In a period from when the display-related processing on the N-th imaging is ended in the display-related processing unit 68 to when the set time elapses, in a case where the (N+1)th imaging is performed, and the irradiation start synchronization signal 79 on the (N+1)th imaging is transmitted from the cassette control unit 67 (in Step ST54, YES), the start of the CAD processing on the N-th imaging is postponed, and the CAD processing is prohibited (Step ST55). In addition, the irradiation start synchronization signal 79 on the (N+1)th imaging is transmitted from the cassette control unit 67 to the electronic cassette 11 (Step ST56). Then, when the irradiation time set in the irradiation conditions 76 has elapsed, the irradiation end synchronization signal 80 on the (N+1)th imaging is transmitted from the cassette control unit 67 to the electronic cassette 11. Subsequently, the image transmission notification signal 87 and the radiographic image 20 on the (N+1)th imaging are received in the image reception unit 85 (Step ST57). The radiographic image 20 on the (N+1)th imaging is output from the image reception unit 85 to the image processing unit 86. Step ST55 is an example of a "priority processing step" according to the technique of the present disclosure.

In the image processing unit 86, the image processing is executed on the radiographic image 20 on the (N+1)th imaging (Step ST19). The radiographic image 20 on the (N+1)th imaging after the image processing is output from the image processing unit 86 to the display control unit 69 and the CAD processing unit 70.

As shown in Step ST58, the display-related processing on the (N+1)th imaging is started at a timing at which the irradiation start synchronization signal 79 on the (N+1)th imaging is transmitted from the cassette control unit 67. Then, the display-related processing on the (N+1)th imaging is ended at a timing at which the radiographic image 20 on the (N+1)th imaging after the image processing is output from the image processing unit 86. Like Step ST53, Step ST58 is an example of a "display-related processing step" according to the technique of the present disclosure.

Figure 41:
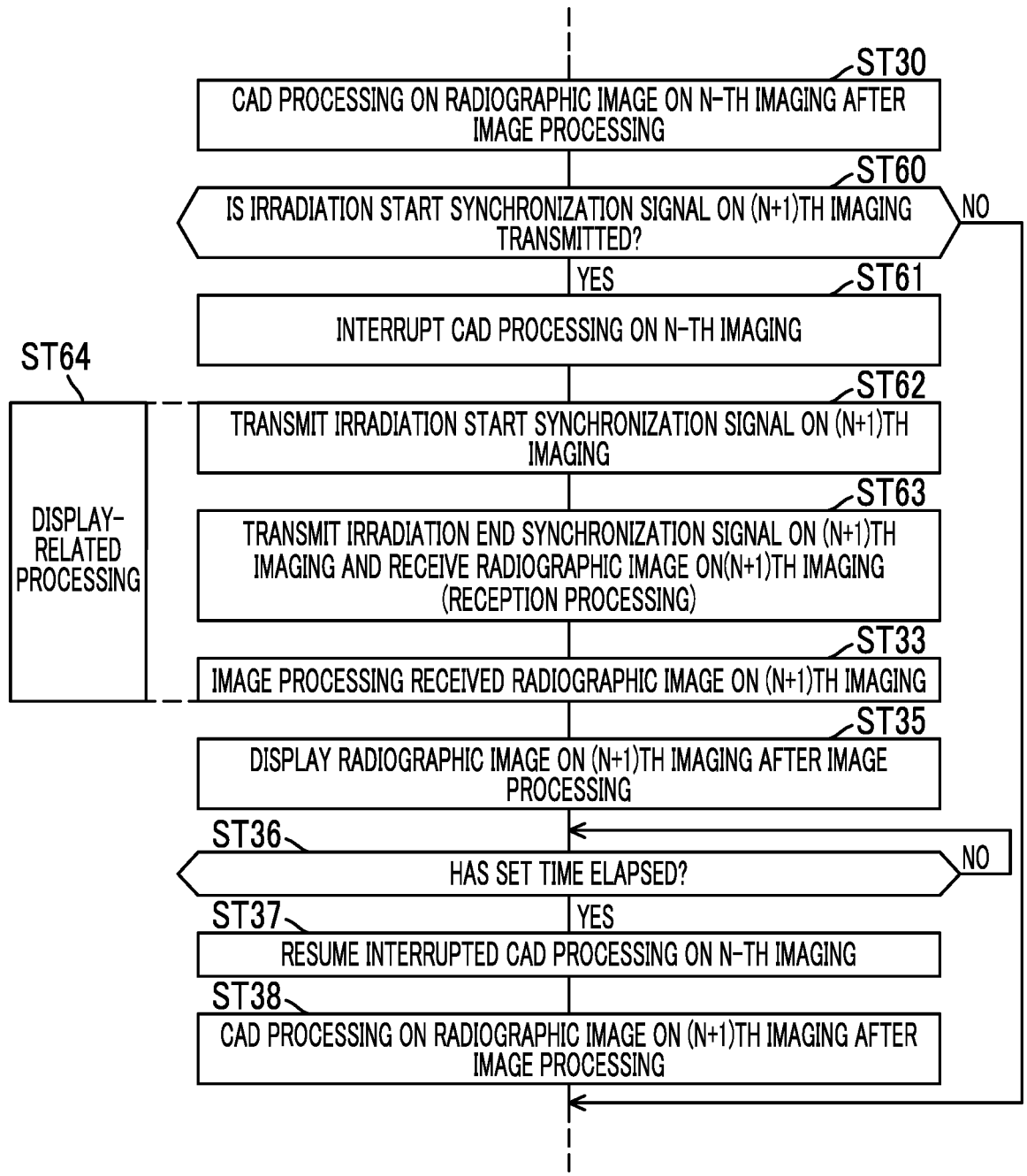
FIG. 41 is a flowchart illustrating the aspect shown in FIG. 39.

FIG. 41 is a flowchart illustrating the aspect shown in FIG. 39. First, in a case where, while the CAD processing on the N-th imaging shown in Step ST30 is being executed, the (N+1)th imaging is performed, and the irradiation start synchronization signal 79 on the (N+1)th imaging is transmitted from the cassette control unit 67 (in Step ST60, YES), the CAD processing on the N-th imaging is interrupted (Step ST61). In addition, the irradiation start synchronization signal 79 on the (N+1)th imaging is transmitted from the cassette control unit 67 to the electronic cassette 11 (Step ST62). Then, when the irradiation time set in the irradiation conditions 76 has elapsed, the irradiation end synchronization signal 80 on the (N+1)th imaging is transmitted from the cassette control unit 67 to the electronic cassette 11. Subsequently, the image transmission notification signal 87 and the radiographic image 20 on the (N+1)th imaging are received in the image reception unit 85 (Step ST63). The radiographic image 20 on the (N+1)th imaging is output from the image reception unit 85 to the image processing unit 86. Like Step ST55, Step ST61 is an example of a "priority processing step" according to the technique of the present disclosure.

In the image processing unit 86, the image processing is executed on the radiographic image 20 on the (N+1)th imaging (Step ST33). The radiographic image 20 on the (N+1)th imaging after the image processing is output from the image processing unit 86 to the display control unit 69 and the CAD processing unit 70.

As shown in Step ST64, the display-related processing on the (N+1)th imaging is started at a timing at which the irradiation start synchronization signal 79 on the (N+1)th imaging is transmitted from the cassette control unit 67. Then, the display-related processing on the (N+1)th imaging is ended at a timing at which the radiographic image 20 on the (N+1)th imaging after the image processing is output from the image processing unit 86. Like Steps ST53 and ST58, Step ST64 is an example of a "display-related processing step" according to the technique of the present disclosure.

In this way, the display-related processing starts at a timing of transmitting the irradiation start synchronization signal 79 for informing of the irradiation start of the radiation R to the electronic cassette 11. For this reason, it is possible to reliably restrain the transmission timings of the irradiation start synchronization signal 79 and the irradiation end synchronization signal 80 from being delayed due to the CAD processing having a comparatively large processing load.

The embodiments other than the first embodiment described above may be applied to the aspect shown in FIG. 37.

Similarly, even the end timing of the display-related processing is not limited to the timing at which the radiographic image 20 is output from the image processing unit 86, illustrated in the drawing. A timing at which the radiographic image 20 is displayed on the display 32 by the display control unit 69 may be defined as the end timing of the display-related processing.

In the respective embodiments described above, although the N-th imaging is an example of "first imaging" according to the technique of the present disclosure, and the (N+1)th imaging is an example of "second imaging" according to the technique of the present disclosure, the technique of the present disclosure is not limited thereto. At least one time of radiography may be interposed between the "first imaging" and the "second imaging".

The cooling fan 56 may be turned off in a case where the CAD processing is not executed, and the cooling fan 56 may be rotated in a case where the CAD processing is being executed, such that the cooling level may be set high while the CAD processing is being executed. In a period from when the CAD processing ends to when a predetermined time elapses, the cooling level of the cooling fan 56 may remain high.

The cooling mechanism is not limited to the cooling fan 56 shown in the drawing, and for example, a Peltier element may be used. A cooling mechanism that is a liquid cooling type, instead of an air-cooling type, may be used.

While the image processing on the N-th imaging is being executed in the image processing unit 86, in a case where the image transmission notification signal 87 of the radiographic image 20 on the (N+1)th imaging is received by the image reception unit 85, the image processing on the N-th imaging may be interrupted, and the reception processing of the radiographic image 20 on the (N+1)th imaging may be given priority.

In the first embodiment described above, although the electronic cassette 11 that performs the accumulation operation in response to the irradiation start synchronization signal 79 and performs the readout operation in response to the irradiation end synchronization signal 80 has been illustrated, the technique of the present disclosure is not limited thereto. An electronic cassette having a function of detecting the irradiation start and the irradiation end of the radiation R by itself may be used. The technique of the present disclosure is not limited to the electronic cassette, and a radiographic image detection device that is installed at an imaging stand may be used.

In the respective embodiments described above, although the console 55 and the like mounted in the mobile radiation generation apparatus 10 have been illustrated, the technique of the present disclosure is not limited thereto. For example, the technique of the present disclosure may be applied to a console mounted in a mammography apparatus that radiographs a breast of the subject H.

In the respective embodiments described above, for example, as the hardware structures of processing units that execute various kinds of processing, such as the reception unit 65, the irradiation control unit 66, the cassette control unit 67, the display-related processing unit 68 (image reception unit 85 and image processing unit 86), the display control unit 69, the CAD processing unit 70, the main control unit 71, and the imaging part specification unit 120, various processors described below can be used. Various processors include a programmable logic device (PLD) that is a processor capable of changing a circuit configuration after manufacture, such as a field programmable gate array (FPGA), and/or a dedicated electric circuit that is a processor having a circuit configuration dedicatedly designed for executing specific processing, such as an application specific integrated circuit (ASIC), in addition to the CPUS 53, 125, 130, and 135 and the GPU 136 that are general-purpose processors configured to execute software (operation program 60 and operation program 141 for CAD processing function expansion) to function as various processing units.

One processing unit may be configured with one of various processors described above or may be configured with a combination of two or more processors (for example, a combination of a plurality of FPGAs and/or a combination of a CPU and an FPGA) of the same type or different types. A plurality of processing units may be configured with one processor.

As an example where a plurality of processing units are configured with one processor, first, as represented by a computer, such as a client or a server, there is a form in which one processor is configured with a combination of one or more CPUs and software, and the processor functions as a plurality of processing units. Second, as represented by system on chip (SoC) or the like, there is a form in which a processor that implements all functions of a system including a plurality of processing units into one integrated circuit (IC) chip is used. In this way, various processing units are configured using one or more processors among various processors described above as a hardware structure.

In addition, the hardware structure of various processors is, more specifically, an electric circuit (circuitry), in which circuit elements, such as semiconductor elements, are combined.

The technique of the present disclosure can also be appropriately combined with at least one of various embodiments or various modification examples described above. The technique of the present disclosure is not limited to the above-described embodiments, and various configurations can be of course employed without departing from the spirit and scope of the technique of the present disclosure. In addition to the program, the technique of the present disclosure extends to a storage medium that stores the program in a non-transitory manner.

The content of the above description and the content of the drawings are detailed description of portions according to the technique of the present disclosure, and are merely examples of the technique of the present disclosure. For example, the above description relating to configuration, function, operation, and advantageous effects is description relating to examples of configuration, function, operation, and advantageous effects of the portions according to the technique of the present disclosure. Thus, it is needless to say that unnecessary portions may be deleted, new elements may be added, or replacement may be made to the content of the above description and the content of the drawings without departing from the gist of the technique of the present disclosure. Furthermore, to avoid confusion and to facilitate understanding of the portions according to the technique of the present disclosure, description relating to common technical knowledge and the like that does not require particular description to enable implementation of the technique of the present disclosure is omitted from the content of the above description and the content of the drawings.

In the specification, "A and/or B" is synonymous with "at least one of A or B". That is, "A and/or B" may refer to A alone, B alone, or a combination of A and B. Furthermore, in the specification, a similar concept to "A and/or B" applies to a case in which three or more matters are expressed by linking the matters with "and/or".

All of the documents, patent applications, and technical standards in the specification are incorporated herein by reference to the same extent that the individual documents, patent applications, and technical standards are described specifically and independently.

What is claimed is:

1. A console for a radiography system comprising:
at least one processor configured to execute;
display-related processing of displaying, at an imaging site, a radiographic image obtained by radiography, the display-related processing including reception processing of receiving the radiographic image from a radiographic image detection device and image processing of processing the received radiographic image to a radiographic image for display,
computer aided diagnosis processing on the radiographic image after the image processing, and
priority processing of giving priority to the display-related processing over the computer aided diagnosis processing in a case where the display-related processing and the computer aided diagnosis processing compete with each other,
wherein the at least one processor is configured to:
interrupt the computer aided diagnosis processing on first imaging and start the display-related processing on second imaging after the first imaging, as the priority processing,
resume the interrupted computer aided diagnosis processing on the first imaging in a case where the second imaging is not reimaging of the first imaging, and
not resume the interrupted computer aided diagnosis processing on the first imaging in a case where the second imaging is the reimaging.

2. The console for a radiography system according to claim 1,
wherein the at least one processor is configured to prohibit the execution of the computer aided diagnosis processing while the display-related processing is being executed, as the priority processing.

3. The console for a radiography system according to claim 2,
wherein the at least one processor is configured to not start the computer aided diagnosis processing on present imaging in a case where the display-related processing on next imaging starts in a period from when the display-related processing on the present imaging ends to when the computer aided diagnosis processing on the present imaging subsequently automatically starts.

4. The console for a radiography system according to claim 1,
wherein the at least one processor is configured to automatically resume the interrupted computer aided diagnosis processing on the first imaging after the display-related processing on the second imaging ends.

5. The console for a radiography system according to claim 1,
wherein the at least one processor is configured to
receive a selection instruction from an operator regarding whether or not to resume the interrupted computer aided diagnosis processing on the first imaging after the display-related processing on the second imaging ends,
resume the interrupted computer aided diagnosis processing on the first imaging in a case where a selection instruction to resume the interrupted computer aided diagnosis processing is received, and
not resume the interrupted computer aided diagnosis processing on the first imaging in a case where a selection instruction not to resume the interrupted computer aided diagnosis processing is received.

6. The console for a radiography system according to claim 1,
wherein the at least one processor is configured to
determine that the second imaging is not the reimaging in a case where an imaging part is not the same as in the first imaging and resume the interrupted computer aided diagnosis processing on the first imaging, and
determine that the second imaging is the reimaging in a case where the imaging part is the same as in the first imaging and not resume the interrupted computer aided diagnosis processing on the first imaging.

7. The console for a radiography system according to claim 1,
wherein the at least one processor is configured to notify an operator that the computer aided diagnosis processing on the first imaging is interrupted.

8. The console for a radiography system according to claim 1,
wherein the at least one processor is configured to receive an execution instruction of the computer aided diagnosis processing from an operator.

9. The console for a radiography system according to claim 1,
wherein the at least one processor that executes the display-related processing and the computer aided diagnosis processing is one processor.

10. The console for a radiography system according to claim 1,
wherein the at least one processor has two sub-processors of a first sub-processor that executes the display-related processing and a second sub-processor that executes the computer aided diagnosis processing.

11. The console for a radiography system according to claim 1,
wherein the at least one processor is configured to start the display-related processing at a start timing of the reception processing.

12. The console for a radiography system according to claim 1,
wherein the at least one processor is configured to start the display-related processing at a timing of transmitting an irradiation start synchronization signal for informing of an irradiation start of radiation to the radiographic image detection device.

13. The console for a radiography system according to claim 1, further comprising:
a cooling mechanism that cools the at least one processor,
wherein the at least one processor is configured to set a cooling level of the cooling mechanism higher than in a normal state at least while the computer aided diagnosis processing is being executed.

14. The console for a radiography system according to claim 1,
wherein the console is mounted in a mobile radiation generation apparatus that has a radiation generation unit configured to emit radiation and is driven with a battery in a wireless manner.

15. A console for a radiography system, comprising:
at least one processor configured to execute:
display-related processing of displaying, at an imaging site, a radiographic image obtained by radiography, the display-related processing including reception processing of receiving the radiographic image from a radiographic image detection device and image processing of processing the received radiographic image to a radiographic image for display,
computer aided diagnosis processing on the radiographic image after the image processing, and
priority processing of giving priority to the display-related processing over the computer aided diagnosis processing in a case where the display-related processing and the computer aided diagnosis processing compete with each other,
wherein the at least one processor is configured to allocate a part of resources allocated to the computer aided diagnosis processing on first imaging to the display-related processing on second imaging after the first imaging and set the number of resources allocated to the display-related processing on the second imaging greater than in the computer aided diagnosis processing on the first imaging, as the priority processing.

16. A method for operating a console for a radiography system, the method comprising:
executing display-related processing of displaying, at an imaging site, a radiographic image obtained by radiography, the display-related processing including reception processing of receiving the radiographic image from a radiographic image detection device and image processing of processing the received radiographic image to a radiographic image for display;
executing computer aided diagnosis processing on the radiographic image after the image processing;
executing priority processing of giving priority to the display-related processing over the computer aided diagnosis processing in a case where the display-related processing and the computer aided diagnosis processing compete with each other;
interrupting the computer aided diagnosis processing on first imaging and start the display-related processing on second imaging after the first imaging, as the priority processing;
resuming the interrupted computer aided diagnosis processing on the first imaging in a case where the second imaging is not reimaging of the first imaging; and
not resuming the interrupted computer aided diagnosis processing on the first imaging in a case where the second imaging is the reimaging.

17. A non-transitory computer-readable storage medium storing an operation program for a console for a radiography system, the operation program causing a computer to:
execute display-related processing of displaying, at an imaging site, a radiographic image obtained by radiography, the display-related processing including reception processing of receiving the radiographic image from a radiographic image detection device and image processing of processing the received radiographic image to a radiographic image for display;
execute computer aided diagnosis processing on the radiographic image after the image processing;
execute priority processing of giving priority to the display-related processing over the computer aided diagnosis processing in a case where the display-related processing and the computer aided diagnosis processing compete with each other;
interrupt the computer aided diagnosis processing on first imaging and start the display-related processing on second imaging after the first imaging, as the priority processing;
resume the interrupted computer aided diagnosis processing on the first imaging in a case where the second imaging is not reimaging of the first imaging; and
not resume the interrupted computer aided diagnosis processing on the first imaging in a case where the second imaging is the reimaging.

* * * * *